US011223915B2

(12) United States Patent
McKinney et al.

(10) Patent No.: US 11,223,915 B2
(45) Date of Patent: Jan. 11, 2022

(54) DETECTING USER'S EYE MOVEMENT USING SENSORS IN HEARING INSTRUMENTS

(71) Applicant: Starkey Laboratories, Inc., Eden Prairie, MN (US)

(72) Inventors: Martin McKinney, Minneapolis, MN (US); Thomas Howard Burns, Minneapolis, MN (US); Yezihalem Mesfin, Farmington, MN (US); Kyle Walsh, Minneapolis, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 0 days.

(21) Appl. No.: 16/799,390

(22) Filed: Feb. 24, 2020

(65) Prior Publication Data
US 2020/0275216 A1 Aug. 27, 2020

Related U.S. Application Data

(60) Provisional application No. 62/832,598, filed on Apr. 11, 2019, provisional application No. 62/810,298, filed on Feb. 25, 2019.

(51) Int. Cl.
*H04R 25/00* (2006.01)
*G06T 7/521* (2017.01)
*G06T 7/70* (2017.01)
*A61B 3/113* (2006.01)
(Continued)

(52) U.S. Cl.
CPC ............ *H04R 25/505* (2013.01); *A61B 3/113* (2013.01); *A61B 5/126* (2013.01); *A61B 5/4094* (2013.01); *A61B 5/7282* (2013.01);
*G06T 7/521* (2017.01); *G06T 7/70* (2017.01); *H04R 25/405* (2013.01); *H04R 25/552* (2013.01);
(Continued)

(58) Field of Classification Search
CPC ....... G06F 3/013; A61B 3/113; A61B 5/4809; A61B 5/6821; A61M 2021/0027; A61M 2230/18
USPC .................................. 381/312, 328
See application file for complete search history.

(56) References Cited

U.S. PATENT DOCUMENTS

| 5,711,308 A | 2/1998 | Singer |
| 10,425,745 B1 | 9/2019 | Merks et al. |

(Continued)

FOREIGN PATENT DOCUMENTS

WO 2019/243768 A1 12/2019

OTHER PUBLICATIONS

Gruters et al., "The eardrums move when the eyes move: A multisensory effect on the mechanics of hearing," PNAS, Proc. Natl. Acad. Sci., Jan. 23, 2018, p. E1309-1318.
(Continued)

*Primary Examiner* — George C Monikang
(74) *Attorney, Agent, or Firm* — Shumaker & Sieffert, P.A.

(57) ABSTRACT

A set of one or more processing circuits obtains eye movement-related eardrum oscillation (EMREO)-related measurements from one or more EMREO sensors of a hearing instrument. The EMREO sensors are located in an ear canal of a user of the hearing instrument and are configured to detect environmental signals of EMREOs of an eardrum of the user of the hearing instrument. The one or more processing circuits may perform an action based on the EMREO-related measurements.

25 Claims, 6 Drawing Sheets

(51) Int. Cl.
*A61B 5/12* (2006.01)
*A61B 5/00* (2006.01)
(52) U.S. Cl.
CPC ......... *H04R 25/604* (2013.01); *H04R 25/609* (2019.05); *G06T 2207/10048* (2013.01); *H04R 2225/41* (2013.01)

(56) References Cited

U.S. PATENT DOCUMENTS

| | | | | |
|---|---|---|---|---|
| 2015/0289065 | A1* | 10/2015 | Jensen | H04R 25/405 |
| | | | | 381/315 |
| 2017/0111747 | A1* | 4/2017 | van Halteren | H04R 25/505 |
| 2019/0038130 | A1 | 2/2019 | Lawrence | |

OTHER PUBLICATIONS

Liang et al., Development of an EOG-Based Automatic Sleep-Monitoring Eye Mask, IEEE Transaction on Instrumentation and Measurement, vol. 64, No. 11, Nov. 2015, pp. 2977-2985.

Woo et al., "A New Trans-Tympanic Microphone Approach for Fully Implantable Hearing Devices," MDPI, Sensors, vol. 15, Sep. 2015, pp. 22798-22810.

"The US Army's new earbuds give soldiers tunable hearing, protection from loud noises," Digital Trends, accessed from https://www.digitaltrends.com/cool-tech/army-noise-canceling-headset/, accessed on Feb. 20, 2019, 11 pp.

Young et al., "Newly Acquired Fear of Falling Leads to Altered Eye Movement Patterns and Reduced Stepping Safety: A Case Study," PLoS ONE, Fear of Falling Alters Eye and Stepping Behaviors, vol. 7, No. 11, Nov. 21, 2012, 7 pp.

Doclo et al., "Chapter 10: Acoustic Beamforming for Hearing Aid Applications, Overview of Noise Reduction Techniques," Handbook on Array Processing and Sensor Networks, Wiley & Sons Inc., Applicant points out, in accordance with MPEP 609.04(a), that the year of publication, 2008, is sufficiently earlier than the effective U.S. filing date, so that the particular month of publication is not in issue.

Di Stassi et al., "Saccadic Eye Movement Metrics Reflect Surgical Residents' Fatigue," Lippincott Williams & Wilkins, Annals of Surgery, vol. 259, No. 4, Apr. 2014, pp. 824-829.

Greany et al., "Saccade to stepping delays in elders at high risk for falling," Aging Clinical and Experimental Research, vol. 20, No. 5, Feb. 6, 2008, pp. 428-433.

Zhao et al., "Miniature implantable low noise piezoelectric diaphragm sound sensor," [abstract only] ASA, The Journal of the Acoustical Society of America, vol. 143, Issue 3, Apr. 17, 2018, 4 pp.

Woo et al., "A New Trans-Tympanic Microphone Approach for Fully Implantable Hearing Devices," MDPI, Sensors, vol. 15, Sep. 9, 2015, 13 pp.

International Search Report and Written Opinion of International Application No. PCT/US2020/019502, dated Jun. 23, 2020, 17 pp.

* cited by examiner

DETECTING USER'S EYE MOVEMENT USING SENSORS IN HEARING INSTRUMENTS

This application claims the benefit of U.S. Provisional Patent Application 62/810,298, filed Feb. 25, 2019, and U.S. Provisional Patent Application 62/832,598, filed Apr. 11, 2019, the entire content of each of which is hereby incorporated by reference.

TECHNICAL FIELD

This disclosure relates to hearing instruments.

BACKGROUND

Hearing instruments are devices designed to be worn on, in, or near one or more of a user's ears. Common types of hearing instruments include hearing assistance devices (e.g., "hearing aids"), earbuds, headphones, hearables, cochlear implants, and so on. In some examples, a hearing instrument may be implanted or osseointegrated into a user. Some hearing instruments include additional features beyond just environmental sound-amplification. For example, some modern hearing instruments include advanced audio processing for improved device functionality, controlling and programming the devices, and beamforming, and some can even communicate wirelessly with external devices including other hearing instruments (e.g., for streaming media).

SUMMARY

This disclosure describes techniques for detecting and performing actions based on eye movement-related eardrum oscillations (EMREOs) of one or more eardrums of a user of one or more hearing instruments. For instance, a set of one or more processing circuits may obtain EMREO-related measurements from one or more EMREO sensors of a hearing instrument. The EMREO sensors are located in an ear canal of a user of the hearing instrument and are configured to detect environmental signals of EMREOs of an eardrum of the user of the hearing instrument. The one or more processing circuits may perform an action based on the EMREO-related measurements.

In one aspect, this disclosure describes a method comprising: obtaining, by a set of one or more processing circuits, eye movement-related eardrum oscillation (EMREO)-related measurements from one or more EMREO sensors of a hearing instrument, wherein the EMREO sensors are located in an ear canal of a user of the hearing instrument and are configured to detect environmental signals of EMREOs of an eardrum of the user of the hearing instrument and generate the EMREO-related measurements based on the detected environmental signals; and performing, by the one or more processing circuits, an action based on the EMREO-related measurements.

In another aspect, this disclosure describes a system comprising: one or more EMREO sensors located in an ear canal of a user of a hearing instrument, wherein the EMREO sensors are configured to detect environmental signals of EMREOs of an eardrum of the user and generate the EMREO-related measurements based on the detected environmental signals; and one or more processing circuits configured to: obtain EMREO-related measurements from the one or more EMREO sensors; and perform an action based on the EMREO-related measurements.

In another aspect, this disclosure describes a system comprising: means for obtaining EMREO-related measurements from one or more EMREO sensors of a hearing instrument, wherein the EMREO sensors are located in an ear canal of a user of the hearing instrument and are configured to detect environmental signals of EMREOs of an eardrum of the user of the hearing instrument and generate the EMREO-related measurements based on the detected environmental signals; and means for performing an action based on the EMREO-related measurements.

In another aspect, this disclosure describes a computer-readable storage medium having instructions stored thereon that, when executed, cause one or more processing circuits to: obtain eye movement-related eardrum oscillation (EMREO)-related measurements from one or more EMREO sensors of a hearing instrument, wherein the EMREO sensors are located in an ear canal of a user of the hearing instrument and are configured to detect environmental signals of EMREOs of an eardrum of the user of the hearing instrument and generate the EMREO-related measurements based on the detected environmental signals; and perform an action based on the EMREO-related measurements.

The details of one or more aspects of the disclosure are set forth in the accompanying drawings and the description below. Other features, objects, and advantages of the techniques described in this disclosure will be apparent from the description, drawings, and claims.

DETAILED DESCRIPTION

Figure 1:
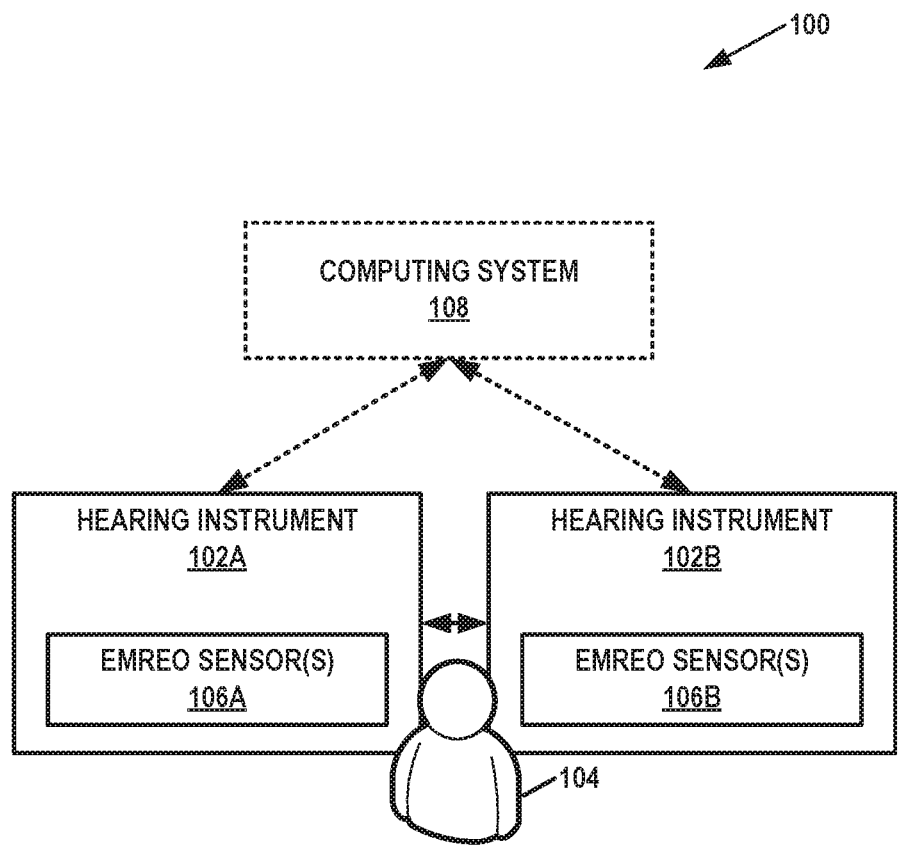
FIG. 1 is a conceptual diagram illustrating an example system that includes one or more hearing instrument(s), in accordance with one or more techniques of this disclosure.

Recent research has demonstrated that eye movements trigger eardrum oscillations. For example, Gruters et al., "The eardrums move when the eyes move: A multisensory effect on the mechanics of hearing," *Proc. Natl. Acad. Sci.*, p. E1309-E1318, 2018, describes this phenomenon as eye movement-related eardrum oscillations (EMREOs). These oscillations produce sinusoidal sound pressure levels in the ear canal of approximately 55 dBA at 35 Hz. Such signals can be measured using otoacoustic emissions (OAEs) testing equipment. Otoacoustic emissions are soundwaves generated within the inner ear that propagate in a lateral (outward) direction through an ear canal.

When the user's eyes move to the left, both eardrums move in sync to the right and then oscillate. When the eyes move to the right, both eardrums move in sync to the left and then oscillate. Eardrum vibration begins approximately 10 milliseconds (ms) before the eyes move and the eardrum vibration continues until shortly after the eyes reach fixation. In other words, EMREOs began as early as 10 ms before saccade onset and lasted throughout the saccade and well into subsequent periods of fixation. The total period of an EMREO is about 110 ms. Significantly, the phase (i.e., direction) of the initial movement of eardrums during an EMREO corresponds to the direction of the eye movement in a horizontal plane. In this context, the horizontal plane is a traverse plane that passes through both of the eyes of the user.

Another aspect of EMREOs is that the amplitude of an EMREO corresponds to the distance the eye moved relative to a fixation point at zero degrees in the horizontal plane. Additionally, EMREOs are detectable even in the presence of sound stimuli (clicks) that are commonly used to elicit OAEs. Moreover, EMREOs occurred in the absence or presence of external sound stimuli but were not triggered nor affected by those sounds. Furthermore, the amplitude of the EMREO was correlated strongly with the distance of the eye movement, and the phase of the EMREO was correlated strongly with the direction of the eye movement. The phase of the EMREO refers to the position of a sound wave relative to a fixed point in time, such as saccade onset. In the context of this disclosure, phase is used to determine whether the pressure change in the ear canal is initially positive or negative in response to an eye movement. Thus, the phase of the EMREO may be considered to be the relative direction of movement of the eardrums at the onset of an EMREO. The frequency of EMREOs is in the 20-40 Hz range.

Currently in a laboratory setting, eye movements are tracked using advanced sensors (e.g., cameras facing the eyes), or electrodes placed in or around the eyes and/or ears that require wired connections and sophisticated amplifiers. Furthermore, although EMREO signals have been measured in a laboratory setting, challenges exist in detecting EMREOs using a microphone in an in-situ hearing instrument due to environmental factors such as user motion, ambient noise, user speech, and other factors.

As described in this disclosure, example hearing instruments may include one or more sensors configured to detect environmental signals of EMREOs, and therefore eye movements. For example, a set of one or more processors may obtain EMREO-related measurements from one or more EMREO sensors of one or more hearing instruments. The EMREO sensors are located in an ear canal of a user of the hearing instrument and are configured to detect environmental signals of EMREOs of an eardrum of the user of the hearing instrument. In this example, the one or more processors may perform an action based on the EMREO-related measurements. For instance, the actions may include changing settings for the hearing instruments, generating information about the sleep of the user, controlling user interfaces, sending interpersonal messages, determining salient objects in the environment of the user, detecting epileptic seizures, and so on. This disclosure also proposes signal-processing and machine-learning techniques that could be used to enhance the measurement of eardrum vibrations and the translation to eye movement information. Furthermore, this disclosure describes techniques that use information about the user's EMREOs to generate health-related data regarding the user. The health-related data may include data related to the user's physical health, mental or emotional health, or a combination thereof.

FIG. 1 is a conceptual diagram illustrating an example system 100 that includes hearing instruments 102A, 102B, in accordance with one or more techniques of this disclosure. This disclosure may refer to hearing instruments 102A and 102B collectively, as "hearing instruments 102." A user 104 may wear hearing instruments 102. In some instances, such as when user 104 has unilateral hearing loss, user 104 may wear a single hearing instrument. In other instances, such as when user 104 has bilateral hearing loss, the user may wear two hearing instruments, with one hearing instrument for each ear of the user.

Hearing instruments 102 may comprise one or more of various types of devices that are configured to provide auditory stimuli to a user and that are designed for wear and/or implantation at, on, or near an ear of the user. Hearing instruments 102 may be worn, at least partially, in the ear canal or concha. One or more of hearing instruments 102 may include behind the ear (BTE) components that are worn behind the ears of user 104. In some examples, hearing instruments 102 comprise devices that are at least partially implanted into or osseointegrated with the skull of the user. In some examples, one or more of hearing instruments 102 is able to provide auditory stimuli to user 104 via a bone conduction pathway.

In any of the examples of this disclosure, each of hearing instruments 102 may comprise a hearing assistance device. Hearing assistance devices include devices that help a user hear sounds in the user's environment. Example types of hearing assistance devices may include hearing aid devices, Personal Sound Amplification Products (PSAPs), cochlear implant systems (which may include cochlear implant magnets, cochlear implant transducers, and cochlear implant processors), and so on. In some examples, hearing instruments 102 are over-the-counter, direct-to-consumer, or prescription devices. Furthermore, in some examples, hearing instruments 102 include devices that provide auditory stimuli to the user that correspond to artificial sounds or sounds that are not naturally in the user's environment, such as recorded music, computer-generated sounds, or other types of sounds. For instance, hearing instruments 102 may include so-called "hearables," earbuds, earphones, or other types of devices. Some types of hearing instruments provide auditory stimuli to the user corresponding to sounds from the user's environmental and also artificial sounds.

In some examples, one or more of hearing instruments 102 includes a housing or shell that is designed to be worn in the ear for both aesthetic and functional reasons and encloses the electronic components of the hearing instrument. Such hearing instruments may be referred to as in-the-ear (ITE), in-the-canal (ITC), completely-in-the-canal (CIC), or invisible-in-the-canal (IIC) devices. In some examples, one or more of hearing instruments 102 may be behind-the-ear (BTE) devices, which include a housing worn behind the ear contains all of the electronic components of the hearing instrument, including the receiver (i.e., the speaker). The receiver conducts sound to an earbud inside the ear via an audio tube. In such examples, the earbud may include EMREO sensors 106A or 106B. In some examples, one or more of hearing instruments 102 may be receiver-in-canal (RIC) hearing-assistance devices, which include a housing worn behind the ear that contains electronic components and a housing worn in the ear canal that contains the receiver.

Hearing instruments 102 may implement a variety of features that help user 104 hear better. For example, hearing instruments 102 may amplify the intensity of incoming sound, amplify the intensity of certain frequencies of the incoming sound, or translate or compress frequencies of the incoming sound. In another example, hearing instruments 102 may implement a directional processing mode in which hearing instruments 102 selectively amplify sound originating from a particular direction (e.g., to the front of the user) while potentially fully or partially canceling sound originating from other directions. In other words, a directional processing mode may selectively attenuate off-axis unwanted sounds. The directional processing mode may help users understand conversations occurring in crowds or other noisy environments. In some examples, hearing instruments 102 may use beamforming or directional processing cues to implement or augment directional processing modes. Example techniques for beamforming are described in U.S. Pat. No. 10,425,745, issued Sep. 24, 2019. Example directional processing cues may include pinna cues, interaural time and level differences, and so on. In some examples, hearing instruments 102 may communicate with an external beamforming device to obtain information about a preferred direction of listening attention.

In some examples, hearing instruments 102 may reduce noise by canceling out or attenuating certain frequencies. Furthermore, in some examples, hearing instruments 102 may help user 104 enjoy audio media, such as music or sound components of visual media, by outputting sound based on audio data wirelessly transmitted to hearing instruments 102.

Hearing instruments 102 may be configured to communicate with each other. For instance, in any of the examples of this disclosure, hearing instruments 102 may communicate with each other using one or more wirelessly communication technologies. Example types of wireless communication technology include Near-Field Magnetic Induction (NFMI) technology, a 900 MHz technology, a BLUETOOTH™ technology, a WI-FI™ technology, audible sound signals, ultrasonic communication technology, infrared communication technology, an inductive communication technology, or another type of communication that does not rely on wires to transmit signals between devices. In some examples, hearing instruments 102 use a 2.4 GHz frequency band for wireless communication. In examples of this disclosure, hearing instruments 102 may communicate with each other via non-wireless communication links, such as via one or more cables, direct electrical contacts, and so on.

In the example of FIG. 1, hearing instrument 102A includes a set of one or more eye movement-related eardrum oscillation (EMREO) sensors 106A and hearing instrument 102B may include a set of EMREO sensors 106B. This disclosure may refer to EMREO sensors 106A and EMREO sensors 106B collectively as "EMREO sensors 106". In other examples of this disclosure, only one of hearing instruments 102 includes EMREO sensors. EMREO sensors 106 may be located within the ear canals of user 104. EMREO sensors 106 may be configured to detect environmental signals of EMREOs of user 104. The environmental signals of EMREOs are signals produced in the environment when EMREOs occur. Example environmental signals of EMREOs may include soundwaves caused by EMREOs, transmission waves through skin of the ear canals of user 104 caused by EMREOs, signals (e.g., structure light signals, reflected laser light, etc.) from which the position and/or shape of the eardrums may be determined, and so on.

As shown in the example of FIG. 1, system 100 may also include a computing system 108. In other examples, system 100 does not include computing system 108. Computing system 108 comprises one or more computing devices, each of which may include one or more processors. For instance, computing system 108 may comprise one or more mobile devices, server devices, personal computer devices, handheld devices, wireless access points, smart speaker devices, smart televisions, medical alarm devices, smart key fobs, smartwatches, smartphones, motion or presence sensor devices, smart displays, screen-enhanced smart speakers, wireless routers, wireless communication hubs, prosthetic devices, mobility devices, special-purpose devices, accessory devices, and/or other types of devices. Accessory devices may include devices that are configured specifically for use with hearing instruments 102. Example types of accessory devices may include charging cases for hearing instruments 102, storage cases for hearing instruments 102, media streamer devices, phone streamer devices, external microphone devices, remote controls for hearing instruments 102, and other types of devices specifically designed for use with hearing instruments 102. Actions described in this disclosure as being performed by computing system 108 may be performed by one or more of the computing devices of computing system 108. One or more of hearing instruments 102 may communicate with computing system 108 using wireless or non-wireless communication links. For instance, hearing instruments 102 may communicate with computing system 108 using any of the example types of communication technologies described elsewhere in this disclosure.

As described in this disclosure, a set of one or more processors (which may include processors in one or more of hearing instrument 102A, hearing instrument 102B, and computing system 108) may obtain EMREO-related measurements from one or more EMREO sensors 106 of one or more of hearing instruments 102. As noted above, EMREO sensors 106 may be located in one or more of the ear canals of user 104 and may be configured to detect environmental signals of EMREOs of one or more of the eardrums of user 104. The processors may perform one or more actions based on the EMREO-related measurements.

Figure 2:
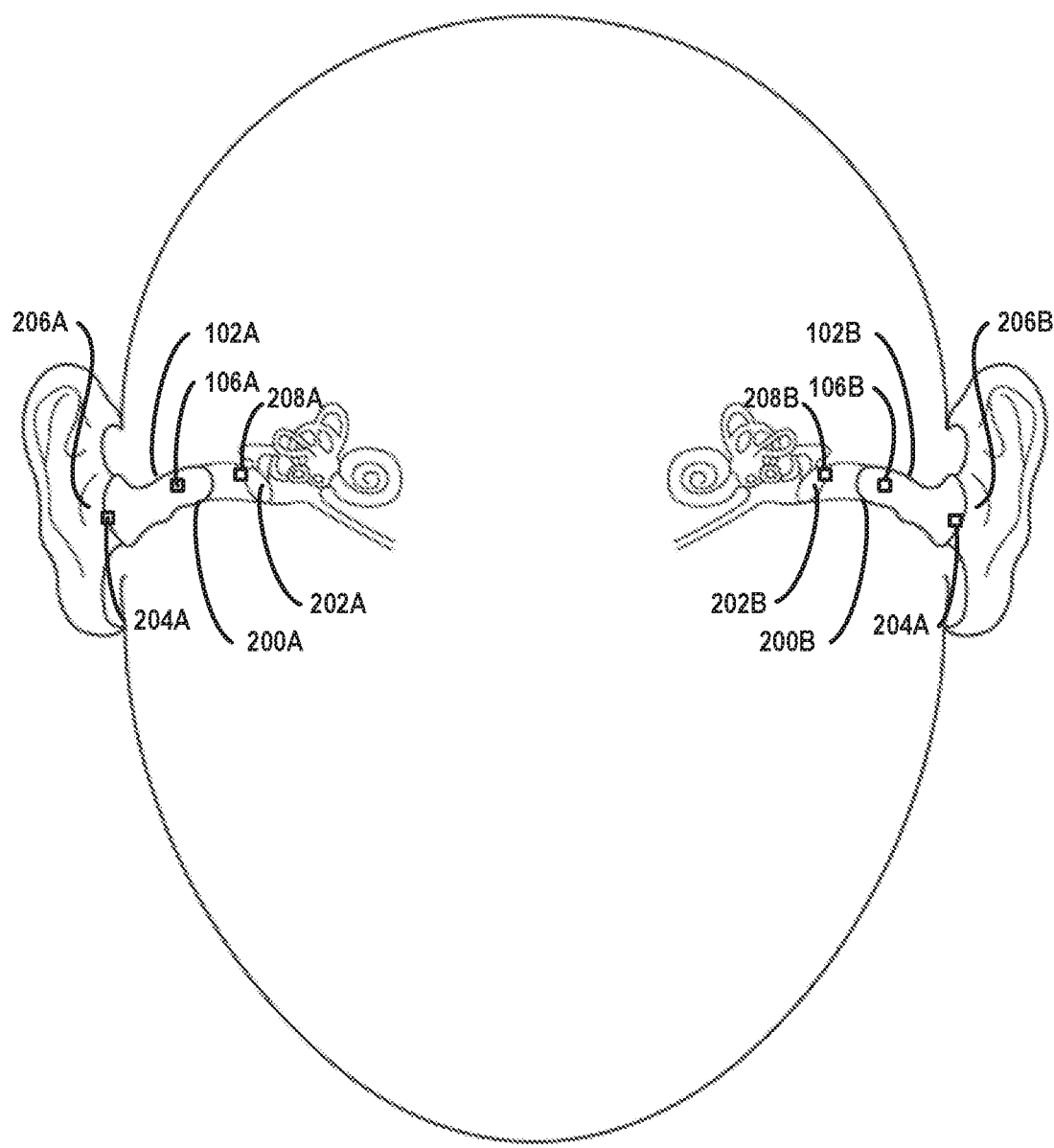
FIG. 2 is a conceptual diagram illustrating example positions of hearing instruments in the ear canals of a user, in accordance with one or more techniques of this disclosure.

FIG. 2 is a conceptual diagram illustrating example positions of hearing instruments 102 in the ear canals 200A, 200B of user 104, in accordance with one or more techniques of this disclosure. This disclosure may refer to ear canals 200A, 200B collectively as "ear canals 200." Eardrums 202A, 202B (collectively. "eardrums 202") are located within ear canals 200. Eardrums 202 may also be referred to as tympanic membranes. As shown in the example of FIG. 2, EMREO sensors 106 may be positioned at the medial tips of hearing instruments 102.

In accordance with one or more examples of this disclosure, hearing instruments 102 may comprise housings that are customized for placement within ear canals 200 of user 104, up to and beyond the second bend to detect EMREOs in situ. In any of the examples of this disclosure, hearing instruments 102 may use signal pre-conditioning and post-processing to acquire reliable EMREO estimates, as described hereinafter with various signal processing methods.

The following section of this disclosure describes a non-limiting set of numbered examples of how EMREO sensors 106 may be implemented. Such examples may be implemented individually or in any combination.

In a first example, EMREO sensors 106A and EMREO sensors 106B each include respective microphone(s) positioned at the (medial) tip of hearing instruments 102. The microphones may measure soundwaves generated by EMREOs that propagate through the air in the ear canals of user 104. In other words, the microphones may be configured to detect changes in air pressure within the ear canals caused by EMREOs.

It is noted that the vibrations evoked by otoacoustic emissions (OAEs) and EMREOs have different characteristics. For example, EMREOs are at lower frequencies than OAEs typically are measured, and EMREOs have larger amplitudes than OAEs. Thus, it is possible to differentiate OAEs and EMREOs in the sounds recorded by microphones in the ear canal. Moreover, EMREOs may be reliably measured even in the presence of click sounds that are used to elicit OAEs.

Beamforming is a technique designed to increase the relative volume of sounds originating from a focal direction relative to other sounds. Thus, beamforming may increase the signal-to-noise ratio with respect to sounds originating from the focal direction. In general, beamforming combines signals synchronously in time from two or more microphones such that correlated sounds (such as those originating from a focal direction (e.g., in front of the listener)) are enhanced and uncorrelated sounds are deemphasized (such as sounds originating from directional other than the focal direction). Thus, beamforming may suppress noise, where noise is considered to be sound not originating from the focal direction. In some examples, beamforming may be implemented in the matter described in Doclo et al., "Acoustic Beamforming for Hearing Aid Applications," Handbook on Array Processing and Sensor Networks, Chapter 10, 2008.

In some examples, EMREO sensors 106A and EMREO sensors 106B each include an array of two or more microphones that are positioned inside the ear canals of user 104 and directed toward the eardrums of user 104. Although they may also serve other purposes, this disclosure may refer to such microphones as EMREO microphones.

In other words. EMREO sensors 106A may include a first array of two or more EMREO microphones and EMREO sensors 106B may include a second array of two or more EMREO microphones. In some such examples, each of hearing instruments 102 may apply beamforming to signals generated by the EMREO microphones of the hearing instrument with the focal direction towards the eardrums of user 104. By applying beamforming, hearing instruments 102 may boost the eardrum vibration signals and reduce the impact of environment sounds.

Thus, in this example, for either or both of hearing instruments 102, the EMREO sensors 106 of the hearing instrument may include a first microphone and a second microphone. The first microphone and the second microphone are positioned within an ear canal of user 104 and may be configured to detect changes in air pressure within the ear canals caused by EMREOs. In this example, EMREO-related measurements may include a first signal produced by the first microphone and a second signal produced by the second microphone. One or more processors (e.g., processors of the hearing instrument, another hearing instrument, and/or computing system 108) may apply a beamformer to the first signal and the second signal to generate a third signal. A focal direction of the beamformer is toward the eardrum of the user of the hearing instrument. Furthermore, in this example, the processors may determine an action to perform based on the third signal.

Furthermore, hearing instruments 102 may temporally align the sound signals from the EMREO microphones and sound signals provided to receivers of hearing instruments 102 and then subtract the sound signals from receivers of hearing instruments from the signals generated by the in-ear EMREO microphones to further reduce the impact of the environmental sounds. In this way, the processors may use multiple microphones in the ear to create a beamformer to enhance the EMREO signal and improve the signal-to-noise ratio (SNR), where the noise is external sound from the environment, or biological noise such as cardiovascular or pulmonary sounds (which also are very low frequency).

Thus, in this example, for either or both of hearing instruments 102, the hearing instrument may comprise an array of external microphones configured to receive sound from an environment of user 104. As part of performing an action based on EMREO-related measurements, a set of one or more processors may determine a focal direction based on the EMREO-related measurements. For instance, the processors may determine the focal direction by first determining a phase of the EMREOs (and hence a direction of eye movements) and a magnitude of the EMREOs (and hence how far the eyes moved in the direction). The processors may then determine the focal direction based on the direction and distance of eye movement. Additionally, the one or more processors may apply a beamformer to signals generated by the external microphones, wherein the beamformer has the determined focal direction. In some examples, the processors may steer a null of the focal direction, which is the direction opposite the focal direction.

In a second example, EMREO sensors 106A and EMREO sensors 106B each include respective medial microphone(s) positioned at the medial tips of hearing instruments 102, hearing instruments 102 may also include lateral microphones 204A, 204B (FIG. 2) positioned at lateral surfaces 206A, 206B (FIG. 2) of hearing instruments 102, such as at faceplates of hearing instruments 102. Processors of hearing instruments 102 may compare the signal(s) from the medial microphones and the lateral microphones to distinguish between ambient noise, user speech, and EMREOs. For example, the sound pressure levels (SPLs) of environmental sounds generated outside the head of user 104 may be larger at lateral microphones 204 than the medial microphones. In contrast, the SPLs from EMREOs may be larger at the medial microphones and smaller, if present at all, at lateral microphones 204. Accordingly, the processors may use these differences in SPLs to distinguish between environmental sounds and pressure changes caused by EMREOs. Furthermore, there may be phase differences between environmental sounds originating outside the head of user 104 and sounds caused by EMREOs. Hence, the arrival of a pressure wave at the medial microphones before lateral microphones 204 may indicate the pressure wave is caused by EMREOs. Additionally, the characteristics of ambient noise, user speech and EMREOs are all different when comparing the signals on the medial and lateral microphones from both ears. EMREOs signals may appear on the medial microphones and occur bilaterally (on both ears relatively simultaneously). Ambient noise signals are typically much stronger on lateral microphones 204 than on the medial microphones and will have a wide array of interaural level and timing differences. User speech typically generates stronger signals on the medial microphones than the EMREOs and may show up synchronous signals across the ears.

Thus, in this second example, for at least one of hearing instruments 102, one or more of the EMREO sensors of the hearing instrument includes a first microphone positioned at a medial tip of the hearing instrument. EMREO-related measurements generated by the EMREO sensors of the hearing instrument may include a signal generated by the first microphone. The hearing instrument may also comprise a second microphone positioned at a lateral surface of the hearing instrument, such as a faceplate of the hearing instrument. Processors of hearing instruments 102 and/or computing system 108 may generate, based on a comparison of the signal generated by the first microphone and a signal generated by the second microphone, an enhanced version of the signal generated by the first microphone. For instance, the processors may compare the signal generated by the first microphone and the signal generated by the second microphone to reduce the impact of noise (e.g., ambient noise from the environment of user 104, user speech sounds, or other types of noise that may mask sounds of EMREOs) in the signal generated by the first microphone. Thus, the enhanced version of the signal generated by the first microphone may have a greater signal-to-noise (SnR) ratio than the original signal generated by the first microphone, where the signal corresponds to air pressure changes caused by EMREOs. The processors may perform one or more actions based on the enhanced signal. For instance, the processors may perform any of the actions set forth elsewhere in this disclosure using the enhanced signal as a set of EMREO-related measurements.

In a third example, EMREO sensors 106A and EMREO sensors 106B each include a respective vertical-cavity surface-emitting laser (VCSEL) and photodetector positioned at the medial tips of hearing instruments 102. In other examples, other types of lasers may be used. For each of hearing instruments 102, the VCSEL of the hearing instrument shines a coherent light beam onto one of eardrums 202 and the photodetector of the hearing instrument detects light reflected by the eardrum. Hearing instruments 102 may use optical feedback interferometry based on the light detected by the photodetector to detect EMREO motion via doppler techniques.

Thus, in this third example, for either or both of hearing instruments 102, the EMREO sensors of the hearing instrument may include a VCSEL positioned to shine a coherent beam onto the eardrum. As part of obtaining EMREO-related measurements, processors of the hearing instrument and/or one or more other devices (e.g., another hearing instrument, devices of computing system 108, etc.) may apply optical feedback interferometry based on reflected light of the coherent beam to determine a position of an eardrum of user 104.

In a fourth example, EMREO sensors 106A and EMREO sensors 106B each include a respective Time of Flight (ToF) sensor and optical lens positioned at the medial tips of hearing instruments 102 such that the ToF sensor system has clear line of sight to the tympanic membrane. The ToF sensor may emit pulses of infrared (IR) light directed at eardrums 106 and the optical lens may detect reflections of the pulses of IR light that are reflected by eardrums 106. The amount of time required for the infrared light to travel from a ToF sensor of a hearing instrument to an eardrum and back to the optical lens of the hearing instrument changes when the distance between the hearing instrument and the eardrum changes. Because the eardrum moves outward and inward during EMREOs, the hearing instrument may detect EMREOs based on changes in the distance between the hearing instrument and the eardrum. In this way, hearing instruments 102 may detect EMREOs based on the arrival of reflected IR energy from the tympanic membrane from an IR pulse emitted from the same sensor system.

Thus, in this fourth example, for either or both of hearing instruments 102, the EMREO sensors of the hearing instrument may include a ToF sensor configured to emit infrared light toward the eardrum and configured to determine a distance to the eardrum based on a travel time of the infrared light to the eardrum and back to the ToF sensor. In this example, as part of obtaining EMREO-related measurements, processors of the hearing instrument and/or one or more other devices (e.g., another hearing instrument, devices of computing system 108, etc.) may determine a position of the eardrum based on the travel time.

In a fifth example, EMREO sensors 106A and EMREO sensors 106B each include a respective fixed structured light (FSL) sensor positioned at the medial tips of hearing instruments 102. In such examples, an FSL sensor emits a fixed structured light pattern that illuminates an eardrum. The structured light pattern may comprise visible light or IR light. The fixed structured light pattern is fixed in the sense that the structure of the light pattern is always the same. For instance, the FSL sensor may project the same pattern of stripes onto the eardrum. The FSL sensor also includes one or more cameras that detect the pattern of light reflected from the eardrum. The hearing instrument may use the patterns of light detected by the one or more cameras to determine a 3-dimensional shape and position of the eardrum. Because the 3-dimensional shape and position of the eardrum changes during an EMREO, the hearing instrument may detect the EMREO based on changes to the determined 3-dimensional shape and position of the eardrum.

In a sixth example, EMREO sensors 106A and EMREO sensors 106B each include a respective programmable structured light (PSL) sensor positioned at the medial tips of hearing instruments 102. A hearing instrument may use a PSL sensor to detect EMREOs in much the same way as described elsewhere in this disclosure with respect to FSL sensors. However, the PSL sensor may be programmed to project different patterns of the structured light. In certain conditions, the PSL sensor is generally capable of detecting depths (i.e., displacements) on the order of microns, whereas in some instance, the FSL sensor can only detect displacements on the order of a millimeter. Thus, PSL sensing may be better depth precision than FSL sensing.

Thus, in the fifth and sixth examples, for either or both of hearing instruments 102, the EMREO sensors of the hearing instrument may include a structured light sensor configured to emit structured light toward the eardrum. As part of obtaining EMREO-related measurements, processors of the hearing instrument and/or one or more other devices (e.g., another hearing instrument, devices of computing system 108, etc.) may determine the position of the eardrum based on a pattern of light detected by the structured light sensor.

In a seventh example, EMREO sensors 106A and EMREO sensors 106B each include one or more vibration sensors that are positioned in the housing of hearing instruments 102 such that the vibration sensor is in contact with the skin of the user's ear canal. EMREO acoustic emissions on the order of 55 dBA also create surface waves that propagate from the eardrum (tympanic membrane), through the skin, and to the vibration sensors of the hearing instrument. Vibration sensor(s) may be of sufficient sensitivity to detect such vibrations while simultaneously rejecting acoustic noise. In other words, the vibration sensor(s) do not primarily detect vibration caused by sounds travelling through the air, but instead primarily detect vibration travelling through the user's skin. In some examples, the vibration sensors belong to a class of sensors that is based on microelectromechanical systems (MEMS) process and aluminum nitride piezoelectric layers. This class of sensors may have a lower input-referred noise floor, thereby allowing sensing of lower signals. In some examples, the vibration sensors may be implemented as described in Grosh, K., et al., "Miniature implantable low noise piezoelectric diaphragm sound sensor," 2pEA4, J. Acoust. Soc. Amer., Vol. 143, No. 3, Pt. 2 of 2, March 2018.

In some examples, hearing instruments 102 may correlate the signals from the vibration sensors with signals from other microphones of hearing instruments 102 and/or any of the aforementioned EMREO detection sensors to acquire reliable estimates. For instance, if a vibration sensor has a strong signal at 35 Hz while a lateral microphone (i.e., a microphone at a surface of a hearing instrument lateral to a midline of user 104) has no 35 Hz signal, then there's a higher probability that saccadic eye movement has occurred. In some examples, hearing instruments 102 may use measures of covariance across different sensors to provide a more robust estimate of the EMREO signal. For instance, in one example, correlating the changes in vibration from the vibrometers and the changes in sound-pressure levels from the in-ear microphone, may provide a more reliable estimate of the movement of the eardrum(s) than an estimate based on either sensor alone. The variance in the estimate is reduced owing to a larger sample size of independent measures.

Thus, in the seventh example, for either or both of hearing instruments 102, the EMREO sensors of the hearing instrument may include a vibration sensor in contact with skin of the ear canal. As part of obtaining EMREO-related measurements, processors of the hearing instrument and/or one or more other devices (e.g., another hearing instrument, devices of computing system 108, etc.) may obtain measurements of surface waves in the skin of the ear canal caused by the EMREOs of the eardrum.

In an eighth example, an implantable vibration sensor is physically attached to the ossicular chain or tympanic membrane of the user such that the processors may use output of the implantable vibration sensor to detect EMREO motion and provide detection results to a cochlear implant or hearing instrument. In this example, the implantable vibration sensor may communicate with the hearing instrument via a wireless or wired-based communication link.

Thus, in the eighth example, for either or both of hearing instruments 102, the EMREO sensors of the hearing instrument may include a vibration sensor (e.g., vibration sensor 208A, 208B of FIG. 2) attached to the eardrum or an ossicular chain of user 104. As part of obtaining EMREO-related measurements, processors of the hearing instrument and/or one or more other devices (e.g., another hearing instrument, devices of computing system 108, etc.) may obtain, by the one or more processors, measurements of vibrations from the vibration sensor.

With the permission of user 104, processors of hearing instruments 102 and/or computing system 108 may use information about the user's eye movements for any of one or more purposes. In other words, the processors may perform one or more actions based on EMREO-related measurements. For instance, the processors may use EMREO-related measurements of user 104 to initiate or augment the processing behaviors of hearing instruments 102. For instance, the processors may use the EMREO-related measurements of user 104 to supplement information from other sensors, such as sensors in hearing instruments 102, that is collected concurrently. The processors may use the resulting information to make inferences about the environment of user 104, the intentions of user 104, physical or mental states of user 104, and so on.

The following section of this disclosure includes a non-limiting set of numbered example use cases. These example use cases may be applied individually or in any combination.

In a first example use case, the processors may use EMREO-related measurements of user 104 to infer a user's activity, such whether they are being social/active, or are focused/stationary. For instance, in one example, the processors may determine the direction of a person's voice using various sound localization techniques. In this example, with the permission of user 104, the processors may determine that user 104 is likely paying attention to the person if the eyes of user 104 track the direction of the person's voice. In some examples, the processors may determine that user 104 is sleeping based on the EMREO-related measurements of user 102 being consistent with the patterns of eye movement associated with the Rapid Eye Movement (REM) phase of the sleep cycle. In some examples, the processors may determine that the user is reading based on the EMREO-related measurements of user 102 corresponding to a reading pattern. The processors may provide such information related to the activity of user 104 to a computing system that generates health-related data based on the information for presentation to user 104 and/or one or more third-party users.

Moreover, in some examples, the processors may use EMREO-related measurements of user 102 to monitor and track sleep patterns and quality of sleep of user 104. In other words, the processors may generate, based on EMREO-related measurements, data regarding sleep of user 104. For example, rapid eye movement (REM) sleep is an important part of sleep. When a person is in REM sleep, the person's eyes move rapidly. In this example, the processors may use EMREO-related measurements of user 102 to infer whether the user is in REM sleep.

The processors may generate various types of health-related data based on information about the user's activity. For example, the processors may generate health-related data that include reports about the quality of sleep that user 104 is getting. In some examples the processors may generate health-related data that provide information about how engaged user 104 is when other people are conversing.

In a second example use case, the processors may use the signals from EMREO sensors 106 to determine whether user 104 is vocalizing. For instance, in addition to using signals generated by EMREO sensors 106 to determine eye movements, the processors may also use signals generated by EMREO sensors 106 to determine whether user 102 is vocalizing. For instance, in an example where EMREO sensors 106 include microphones located at the medial tips of hearing instruments 102, the processors may compare the signals from these microphones for each ear to determine whether sounds originated from a direction between the ears of user 104. In some examples where EMREO sensors 106 include vibration sensors, the processors may determine whether the user is vocalizing based on vibration signals generated by the vibration sensors. For instance, vibrations caused by vocalizations of user 104 may arrive at the vibration sensors concurrently, while vibrations caused by sound may arrive at the left and right ears at different times. Thus, in this example, the processors may compare timing data of vibration signals detected by the vibration sensors to determine whether user 104 is vocalizing.

In a third example use case, the processors may use EMREO-related measurements of user 102 to infer information about a mental state of user 104, such as their level of attention. For instance, in one example, the processors may use EMREO-related measurements of user 104 to determine whether user 104 is looking in the direction of a person who is speaking. In another example, the processors may use EMREO-related measurements of user 104 to determine, with the permission of user 104, whether user 104 is looking forward while walking, running, driving, or otherwise moving. This, potentially in combination with information about the head pose of user 104, may help determine whether user 104 is paying attention to what may be occurring in front of user 104. The processors may provide information about the mental state of user 104 to a computing system that generates health-related data based on the information for presentation to user 104 and/or one or more third-party users.

In another example, the processors may use EMREO-related measurements of user 104 to determine whether user 104 is tired or fatigued. For instance, studies have suggested that subjective fatigue is associated with decreased saccadic velocity. See e.g., Di Stasi et al., "Saccadic eye movement metrics reflect surgical residents' fatigue," Ann. Surg. April 2014; 259(4); 824-9. In other words, when a person feels fatigued, the person's eyes may move slower. Because the speed of eye movements of user 104 may be determined from EMREOs, the processors may use EMREO-related measurements to estimate the level of fatigue of user 104. For example, the processors may establish a normative range of values of eye-movement velocities for user 104. Subsequently, in this example, the processors may compare current velocities to the established normative range of values to determine if they are indicative of a state of fatigue. In some activities, the user's increased levels of fatigue are correlated with increased error rates. For instance, operators of heavy machinery, such as semi-trucks and mining equipment, are more likely to have accidents if they are tired. The processors may use estimates of the level of fatigue of user 104 to generate warnings to user 104 and/or other persons, generate logs for regulatory purposes, or other functions. It is also noted that many of the activities in which there is a correlation between fatigue and error also involve exposure to excessive noise. Accordingly, hearing instruments 102 may also be configured to provide hearing protection and/or log noise exposure levels.

In a fourth example use case, the processors may use EMREO-related measurements of user 102 to infer salient objects in the environment of user 104. In other words, the processors may determine, based on EMREO-related measurements, a salient object in an environment of user 104. For instance, the processors may determine, based on EMREO-related measurements, a direction of gaze of user 104. For instance, if the EMREO-related measurements indicate EMREOs corresponding to an eye movement 45-degrees to the left of the center of user 104, the processors may determine that the salient object is located in a direction 45-degrees to the left of the center of user 104. In some examples, the processors may apply a neural network or other technique for image recognition to identify objects. Many image recognition techniques are known in the art. Furthermore, in some examples, the processors may enable user 104 to indicate which of the one or more identified objects are salient. In some examples, the processors may automatically determine, based on one or more heuristics, which of the identified objects are salient. For instance, the processors may use a neural network-based algorithm or business-rule based algorithm to determine which identified objects are most likely to be considered salient.

For example, user 102 may wear one or more cameras that capture the field of view of user 104. For instance, the cameras may be embedded in an MR or AR visualization device worn by user 104, embedded in eyewear worn by user 104, worn on a chest or shoulder of user 104, held in a hand of user 104, etc. In this example, the processors may determine which objects or areas in the images captured by the cameras are salient to user 104 based on the direction of the gaze of user 104. In some examples, the processors may communicate information about the salient objects or areas to one or more other devices. For instance, a device may present video from perspective of user 104 and visually indicate in the video which objects or areas are salient to user 104.

In a fifth example use case, the processors may use EMREO-related measurements of user 102 to control user interfaces (e.g., volume and memory controls, playback controls for media (e.g., play, pause, skip track, change channel, etc.)). In other words, the processors may determine user input to a user interface based on the EMREO-related measurements. For example, user 104 may wear a headset that presents virtual reality (VR), mixed reality (MR), or augmented reality (AR) visualizations to user 104. In this example, visualizations may include interactive virtual features, such as virtual menus, virtual icons, virtual buttons, and virtual objects. In examples where the headset presents MR or AR visualizations to user 104, user 104 may also be able to see real objects. In this example, the processors may determine, based on the movements of the eyes of user 104 where the user is looking at one of the virtual features or a real object. This may enable the processors to perform some action based on the virtual or real object at which user 104 is looking. For instance, in one example, the virtual features may include an "up" element positioned at the right side of field of view of user 104 and a "down" element positioned at the left side of the field of view of user 104. Thus, in this example, the processors may increase a volume level of hearing instruments 104 when user 104 looks right and decrease the volume level of hearing instruments 104 when user 104 looks left. In another example, the virtual features include "previous" and "next" elements and the processors may change with item is highlighted in a virtual menu of items based on whether user 104 looks left or right.

In other examples where the processors use EMREO-related measurements of user 102 to control user interfaces, the user interface is a voice interface. For instance, in one such example, one or more of hearing instruments 102 may provide an auditory stimulus to user 104 that prompts user 104 to look in a particular direction (e.g., left or right) in order to provide input to the processors. For instance, hearing instruments 102 may generate sound asking user 104 to look left to change an acoustic profile of hearing instruments 102 or to keep the current acoustic profile of hearing instruments 102.

In a sixth example use case, the processors may use EMREO-related measurements of user 102 to augment the detection of falls. Falls are a leading cause of injury and death, especially among the elderly. Receiving prompt medical attention after a fall may be critical in achieving positive health outcomes for a person who has fallen. Accordingly, various techniques for automatically detecting falls have been developed, including techniques that use signals from one or more sensors included in hearing instruments.

For instance, in one example of the sixth use case, the processors may implement a machine learning system, such as an artificial neural network. In this example, the machine learning system may receive EMREO-related measurements as input and may generate output data that provides information about whether user 104 has fallen. For example, the output data may include a confidence level that indicates a level of confidence that user 102 has fallen. In some examples, the output data may indicate in a binary manner whether user 102 has fallen. In some examples, the output data may include data indicating an estimated severity of the fall. The machine learning data may be trained on matched pairs of (i) input data (which, in accordance with techniques of this disclosure, includes EMREO-related measurements), and (ii) data indicating whether the input data coincided with a fall. In some examples, the input to the machine learning system may include EMREO-related measurements and also include other data, such as data from an IMU, data from a photoplethysmography sensor, data from an EKG sensor, data from one or more microphones, and so on. The machine learning system may use all of these types of data in determining the output data. Including the EMREO-related measurements in the input data may make fall detection more robust, which may result in fewer false positives and fewer false negatives.

In a seventh example use case, the processors may use EMREO-related measurements of user 102 to assess the susceptibility of user 102 to falling. Research has demonstrated that there are relationships between eye movement patterns and errors in foot placement during walking or running. For example, persons who recently fell are more likely to fall again due in part to changes in eye movements after a fall, namely less fixation on current foot position and more fixation on upcoming objects, which may lead to errors in stepping. For instance, in this example, if a person trips and falls on any icy sidewalk, the person may be more likely to be looking ahead from additional icy spots and not notice a change in the angle of the sidewalk, resulting in another fall. Accordingly, in an example of the seventh use case, the processors may use EMREO-related measurements of user 102 to assess whether the eye movements of user 102 are consistent with the user 102 looking for upcoming object and not looking at current foot placement.

In another example, the coordination between eye movements and foot placements was impaired in older adults who had a history of falls compared to older adults who had not fallen previously. Accordingly, in an example of the seventh use case, the processors may use EMREO-related measurements of user 102 to determine the fall risk of user 102 based on a pattern of eye movements and foot steps of user 102.

In either example or other examples of determining the susceptibility of user 102 to falling, the processors may implement a machine learning system, such as an artificial neural network, that receives input data that includes EMREO-related measurements and data (e.g., IMU data) indicating footfalls of user 102. In this example, the machine learning system may generate output data that includes data indicating a susceptibility of user 102 to falling. For instance, the output data may include a fall risk score for user 102. The machine learning system may be trained in one of a variety of ways, such as by using training data that specifies pairs input data and correct output data.

The processors may use information about the susceptibility of user 102 to falling in one or more of various ways. For instance, in some examples, the processors may determine, based on the susceptibility of user 102 to falling risk, whether to notify patients, doctors, loved ones, or other people about the presence of a fall risk, or a trend towards increased risk. The processors may store data regarding the susceptibility of user 102 to falling for purposes of determining whether a trend towards increased risk is occurring.

In an eighth example use case, the processors may use EMREO-related measurements of user 102 to detect epileptic seizures or diagnose epilepsy. In other words, the processors may detect, based on EMREO-related measurements, an epileptic seizure of user 104. For instance, when a person suffers an epileptic seizure, the person's eyes may move rapidly. Furthermore, people with epilepsy may have patterns of eye movements that are different from people who do not have epilepsy. Hence, the processors may use EMREO-related measurements of user 102 to determine whether user 104 is experiencing an epileptic seizure or possibly has epilepsy.

In a ninth example use case, the processors or humans may use EMREO-related measurements of user 104 to supplement information provided by concurrent and covarying signals collected by hearing instruments 102 or other sensor devices, such as acoustic information, patterns of vibration on the skin of the ear canal, electroencephalography (EEG), electrooculography (EOG), accelerometer data, gyroscope data, etc.

For instance, in the ninth use case, the processors or humans may use EMREO-related measurements of user 102, EEG signals, respiration rate, respiration patterns, heart rate, heart rhythms, vocalizations of user 102. IMU data (e.g., accelerometer data and gyroscope data), snoring, body temperature, environmental temperature, environmental humidity, environmental noise, environmental light levels, and other information to detect sleep problems. For instance, the processors of hearing instruments 102 and/or computing system 108 may use such information as input to a neural network algorithm or business rule-based algorithm that diagnoses sleep problems.

Sleep problems are a common complaint. Diagnosing sleep problems typically requires a patient to sleep at a sleep clinic that has specialized equipment. Visits to sleep clinics are typically expensive and disruptive to the patient's routine. Moreover, for many patients, the type of sleep the patients have at a sleep clinic is not representative of the type of sleep the patients have at home because of the unfamiliar setting of sleep clinic, because of the feeling of being observed, and so on. However, much of the information collected during a visit to a sleep clinic may be collected instead by sensors in hearing instruments 102. Thus, a patient (e.g., user 104) may take hearing instruments 102 home and sleep there for one or more nights instead of at a sleep clinic. This may enable more healthcare professionals to get more representative data regarding the sleep patterns of the patient. Being able to get more representative data regarding the sleep patterns of the patient may be especially useful in identifying and treating sleep disorders that happen only occasionally, such as somnambulism and night terrors. Gathering information about REM sleep is one component of performing a sleep exam. As discussed elsewhere in this disclosure, EMREO-related measurements may be used to detect REM sleep. Thus, in this way, the one or more processors may generate, based on EMREO-related measurements, data regarding sleep of user 104, such as the lengths of time user 104 spends in REM sleep/non-REM sleep, times of onset of REM sleep/non-REM sleep. The data regarding sleep of user 104 may include data based on other sensors in hearing instruments 102, such as IMU signals for determining restlessness during sleep, breathing rates and patterns (e.g., for detecting sleep apnea), microphone signals for detecting snoring, and so on.

In another example of the ninth use case, the processors or humans may use EMREO-related measurements of user 104 to conduct sobriety testing (e.g., in the context of traffic stops). In this example, impaired persons may exhibit horizontal gaze nystagmus and poor balance. Horizontal gaze nystagmus is a type of involuntary jerking eye movement. EMREO sensors 106 may generate EMREO-related measurements that provide empirical evidence of horizontal gaze nystagmus. Additionally, IMUs in hearing instruments 102 may generate empirical evidence of balance problems. Generation of such empirical evidence may reduce the reliance of the subjective judgment of law enforcement officers. In some examples, the processors may apply one or more algorithms (e.g., neural network algorithms, business rule algorithms, etc.) that take as input EMREO-related measurements of user 104 and other input data to generate scores or other output to indicate results of a sobriety test. In some examples, other types of data are not used in the sobriety test.

In a tenth example use case, the processors may use EMREO-related measurements of user 104 to adaptively change the signal-processing behavior of cochlear implants by detecting vibration on the ossicular chain or on the skin of the ear canal. For example, many of use cases described in this disclosure may be applied with respect to cochlear implants, including application of beamforming with steering of a focal direction (directional beam) in a direction of eye fixation, or the adjustment of volume based on the gaze behavior of the user.

In an eleventh example use case, the processors may use EMREO-related measurements of user 104 to determine the placement of an allocentric sound source. An allocentric sound source is a sound source that originates from a location near the center of a group of people, as is frequently the case for theatres and concert venues. Consider for example a situation in which an orchestra is performing on a stage. Typically, in such situations, there is a set of microphones positioned near or above the orchestra to detect sound generated by performers of the orchestra. The microphones are generally positioned and balanced to capture sound as that sound would be perceived by a person centered in front of the stage. Signals generated by the microphones may be transmitted to hearing instruments 102. In this way, user 104 may be able to better hear the sound generated by the orchestra than when hearing instruments 102 process sound detected by microphones of hearing instruments 102. However, user 104 may not actually be centered in front of the orchestra. Moreover, user 104 might not always have their head turned to look at the orchestra. Thus, user 104 may perceive the sounds produced by the orchestra to always originate from a point in space in front of user 104, regardless of where user 104 is with respect to the orchestra and regardless of the direction in which user 104 is looking. This may be disorienting to user 104 or may reduce the enjoyment of user 104.

Hearing instruments 102 may be configured to correct this problem by modifying a left-ear signal and a right-ear signal. For instance, in the example above, if the orchestra is to the left of user 104, hearing instruments 102 may introduce a delay and reduce the intensity of the right-ear signal, thereby causing user 104 to perceive the sound of the orchestra to be coming from the left of user 104. The processors may determine the amount of delay and/or intensity modification to introduce using mathematical models based on the angle of origin of the sound relative to a sagittal plane of user 104. For instance, the processors may apply Head-Related Transfer Functions (HRTFs) that describe the relative relationship of sound signals hitting the two eardrums for any given sound-source location relative to the listener.

However, there are challenges associated with techniques for correcting the sound in this manner. For instance, requiring user 104 to manually indicate the angle of their head relative to the actual sound source may be time consuming and awkward for user 104. Furthermore, hearing instruments 102 may be able to determine the angle of the head of user 104 relative to the actual sound source based on IMU signals related to the movement of the head of user 104. However, because of the time required to determine this angle based on the IMU signals, there may be a delay between when user 104 moves their head and when hearing instruments 102 are able to modify the left-ear and right-ear signals to compensate for the change in angle between the head of user 104 and the actual sound source. This may result in user 104 feeling that the actual, visually-perceived origin point of the sound of the orchestra is not synchronized with the audibly-perceived origin point of the sound of the orchestra as perceive. In fact, user 104 may get the sensation that the audibly-perceived origin point of the sound is chasing after the actual, visually-perceived origin point of the sound.

It is noted that people generally move their eyes in a direction before turning their heads to look in that directions. Additionally, it is noted that during an EMREO, the eardrums begin to vibrate before the eyes actually move. Thus, there is a time delay between when the eardrums being to vibrate and when the head of user 104 actually moves. This time delay may provide sufficient time for the processors to determine how to modify the left-ear signal and the right-ear signal before the user actually turns their head to toward the sound source. Determining how to modify the left-ear signal and the right-ear signal before the user actually turns their head to toward the sound source may improve the experience of the user because it may help to eliminate the delay between the time when the user turns their head and the time when hearing instruments 102 start modifying the left-ear signal and the right-ear signal. In this way, user 104 may not get the sensation that the audibly-perceived origin point of the sound is chasing after the actual, visually-perceived origin point of the sound as user 104 turns their head. It is noted that user 104 might glance to one side but not actually turn their head to follow the glance. Nevertheless, it may be worthwhile determining how to modify the left-ear and right-ear signals in case user 104 does follow through and move their head.

Thus, in some such examples, the processors may determine, based on the EMREO-related measurements, potential modifications to left-ear and right-ear audio signals. Additionally, the processors may apply the potential modifications to the left-ear and right-ear audio signals in response to determining a movement of a head of the user. In such examples, it may be assumed that the eyes of user 104 are oriented in the direction of attention of user 104, and that is where attended sounds originate. By inferring this, the polar pattern of directional hearing aids can be steered so that sounds coming from that direction are emphasized and sounds from other directions are deemphasized (e.g., by applying beamforming).

In a twelfth example use case, the processors may use EMREO-related measurements of user 104 to select a directional processing mode. For example, users of hearing instruments commonly struggle to understand speech in loud ambient noise and may rely on reading a person's lips to augment intelligibility. This is often referred to as the 'cocktail party' effect. To address this cocktail party effect, hearing instruments 102 may be configured to use directional processing modes to attenuate sounds arriving from locations other than a location of a person to whom user 104 wants to listen. For instance, if the person to whom user 104 wants to listen is directly in front of user 104, hearing instruments 102 may attenuate sounds arriving from all other directions than directly in front of user 104. Similarly, if the person to whom user 104 wants to listen is directly in left of user 104, hearing instruments 102 may attenuate sounds arriving from all other directions than to the left of user 104.

Hearing instruments 102 have traditionally relied upon receiving indications of user input to indicate whether user 104 is in a situation in which a directional processing mode is desired and to indicate the direction of the sounds to which user 104 wants to listen. Alternatively, hearing instruments 102 may rely on the head movements of user 104 to determine a direction of the sounds to which user 104 wants to listen. Similar to the examples provided above with respect to allocentric sounds, providing such input or relying on head movements may introduce distracting delays. Moreover, relying on head movements for directional processing may require user 104 to actually move their head to the direction of the person to whom user 104 wants to listen. In real life, people do not always turn their head to look at the person to whom they want to listen. Rather, people frequently just move their eyes to look at the person to whom they want to listen.

As noted above, during EMREOs, the eardrums may begin to move prior to the eyes of user 104 beginning to move. Hence, the processors may have sufficient time to determine how to adapt the directional processing mode and then to adapt the directional processing mode accordingly to enhance the perceptibility of sounds arriving from the direction that user 104 is about to look. Thus, if multiple people are speaking around user 104, detecting eye movements of user 104 via EMREOs may provide insight into optimal settings for hearing instruments 102. For instance, in this example, if the EMREOs of user 104 suggest that user 104 is looking to the right or about to look to the right, hearing instruments 102 may use a directional processing mode to attenuate sounds arriving from directions other than the rightward direction. In any of the examples of this disclosure, the processors may use EMREO data to steer a microphone beamformer, or to select from a set of pre-designed beamformers, or to determine a primary lobe width of an adaptive beamformer. For instance, in one example, the processors may determine the primary lobe width based on the range of eye movements over a set amount of time over which that calculation is made, the range being the distance along the azimuth between the leftmost eye movement and the rightmost eye movement. In the examples above that use pre-designed beamformers, each of the pre-designed beamformers may have different focal directions and/or primary lobe widths. In this way, beamformer steering may begin before the eyes move, thus reducing the latency between eye movement and beam steering.

In a thirteenth example use case, the processors may use EMREO-related measurements of user 104 to facilitate interpersonal communication. Thus, the one or more processors may determine an interpersonal message based on EMREO-related measurements and may send the interpersonal message. Using EMREO-related measurements of user 104 to facilitate interpersonal communication may be especially valuable in situations where it is impractical or undesirable to communicate verbally, manually (e.g., with hand gestures), keyboards, or touchscreens. Accordingly, hearing instruments 102 may be configured for wireless communication (or may be communicatively coupled using a wireless- or non-wireless communication technology to another device that is configured for inter-device communication). In this example, user 104 may perform a series of eye movements that correspond to a message that user 104 wants to convey. EMREO sensors 106 may detect EMREOs corresponding to the series of eye movements. The processors may then cause hearing instruments 102 to send data representing the message.

Sending a message in this way may be useful in any of a variety of scenarios. Consider, for example, a firefighter who is battling a fire. The sound of the fire and their equipment may prevent verbal communication and the firefighter might have their hands full with firefighting equipment. In this example, the firefighter wearing hearing instruments 102 may use a series of intentional eye movements to generate a message that hearing instruments 102 communicate to devices associated with one or more other users, such as the firefighter's colleagues.

User 104 may use eye movements to generate a message in one or more of various ways. For instance, in one example, user 104 may use a series of glances that encode information in a manner similar to Morse code. Morse code is a character encoding scheme that uses sequences of different signal durations (dots and dashes) to represent characters, such as letters and numbers. In this example, short glances in a direction may correspond to dots and long glances in the same direction may correspond to dashes. In another example, glances to the right may correspond to dots and glances to the left may correspond to dashes. In some examples, sequences of long or short glances, glances left or right, or combinations thereof may be used to encode characters, full words, phrases, or concepts.

In another example of how user 104 may use eye movements to generate a message, a user interface presented to user 104 (e.g., a voice interface, an MR visualization, etc.) may provide user 104 with a set of options. These options may include words, phrases, categories, etc. User 104 may perform eye movements to select one or more options in order to form a message. In some examples, the processors may use prediction techniques to select the options. For instance, given that user 104 selected an option corresponding to a first word, the processors may provide options indicating words that are likely to follow the first word. Such prediction techniques are commonly found in smartphone virtual keyboards.

One or more of the use cases described in this disclosure may find application in various scenarios. For instance, in one example, consider that user 104 may be a member of a group. The people in the group may not want to speak for any of a variety of reasons. At the same time, the people may be unable to see hand gestures because of obstacles, or may be unable to use hand gestures, keyboards, or touchscreens because their hands are otherwise occupied. In this scenario, user 104, may perform an intentional series of eye movements that correspond to a message that user 104 wants to convey to the other people in the group. For instance, user 104 may want to convey a message about their plans or request help. In this example, hearing instruments 102 may export data corresponding to the message for wireless transmission. In some examples, devices receiving the message may use visual, audible, and/or tactile/haptic output to present the message to persons associated with the receiving devices.

Temporary or permanent hearing loss caused by loud sounds is an issue confronting people in a variety of occupations. For instance, the sounds of the equipment used by or near user 104 may prevent the person from receiving audibly-conveyed information. At the same time, conventional earplugs or sound protection ear muffs may also prevent user 104 from hearing audibly-conveyed commands or from hearing the movements of allies and enemies. Moreover, exposure to loud sounds may lead to tinnitus.

Tinnitus and permanent hearing loss impose significant financial burdens on healthcare systems. Accordingly, earplugs have previously been introduced that provide hearing protection by reducing high-decibel sounds while allowing the users to hear lower-decibel sounds. Advantageously, hearing instruments 102 that offer such hearing protection may also detect EMREOs and use information about users' eye movements (e.g., EMREO-related measurements) for any of the purposes described in this disclosure. For instance, hearing instruments 102 may offer hearing protection and enable users to send interpersonal messages.

Furthermore, consider a scenario as discussed above with respect to the fourth example use case where the processors may use EMREO-related measurements of user 102 to determine salient objects or areas in the environment of user 104. In this scenario, a group of users may wear or otherwise use MR visualization devices and cameras that capture the fields of views of the users. It may be difficult for a first user to quickly explain the location of an object of interest to her fellow users. In accordance with a technique of this disclosure, the MR visualization devices of fellow users may include windows showing the first user's field of view. The first user may fixate her gaze on the object of interest. EMREO sensors 106 may detect signals of EMREOs associated with the first user moving her eyes to fixate on the object of interest. The processors may determine, based on EMREO-related measurements of the first user, a location of the object of interest within the first user's field of view and mark that location within the windows presented by the MR visualization devices of the other users. In this example, the first user may also use eye gestures as previously discussed to communicate information to her follow users.

Communication security is also of great importance in some scenarios. For example, a user may obtain a communication tool, such as a radio, belonging to another user. In this scenario, the user may use the communication tool inappropriately. Techniques of this disclosure may reduce the risk of this scenario occurring. For instance, as described elsewhere in this disclosure, hearing instruments 102 may include a variety of sensors, including EMREO sensors 106 and may be used to send interpersonal messages. Should the processors determine that the signals from such sensors represent the presence or absence of particular types of signals (e.g., absence of heart rate signal, absence of EMREOs, etc.), hearing instruments 102 may disable one or more capabilities (e.g., inter-personal communication capabilities) of hearing instruments 102, thereby preventing hearing instruments 102 from being used by a person other than an authorized user.

In accordance with some examples of this disclosure, in-ear and/or around-the-ear electrodes may be used employed together with EMREO-related measurements to more robustly detect and track eye movements. For example, electrooculography (EOG) is a technique in which electrodes placed on a person's head or face may detect electrical signals associated with eye movements. In general, the electrical signals contain more noise when the electrodes are placed within the person's ears and contain less noise when the electrodes are placed closer to the person's eyes. Thus, it may be more difficult to determine the person's eye movements based on signals from electrodes that are placed within the person's ears than from electrodes that are placed close to the person's eyes. However, placement of electrodes close to a person's eyes has negative practical and aesthetic consequences. For instance, electrodes positioned on a person's face are easily knocked off during activities or during sleep and may not have an acceptable appearance for typical use.

Figure 3:
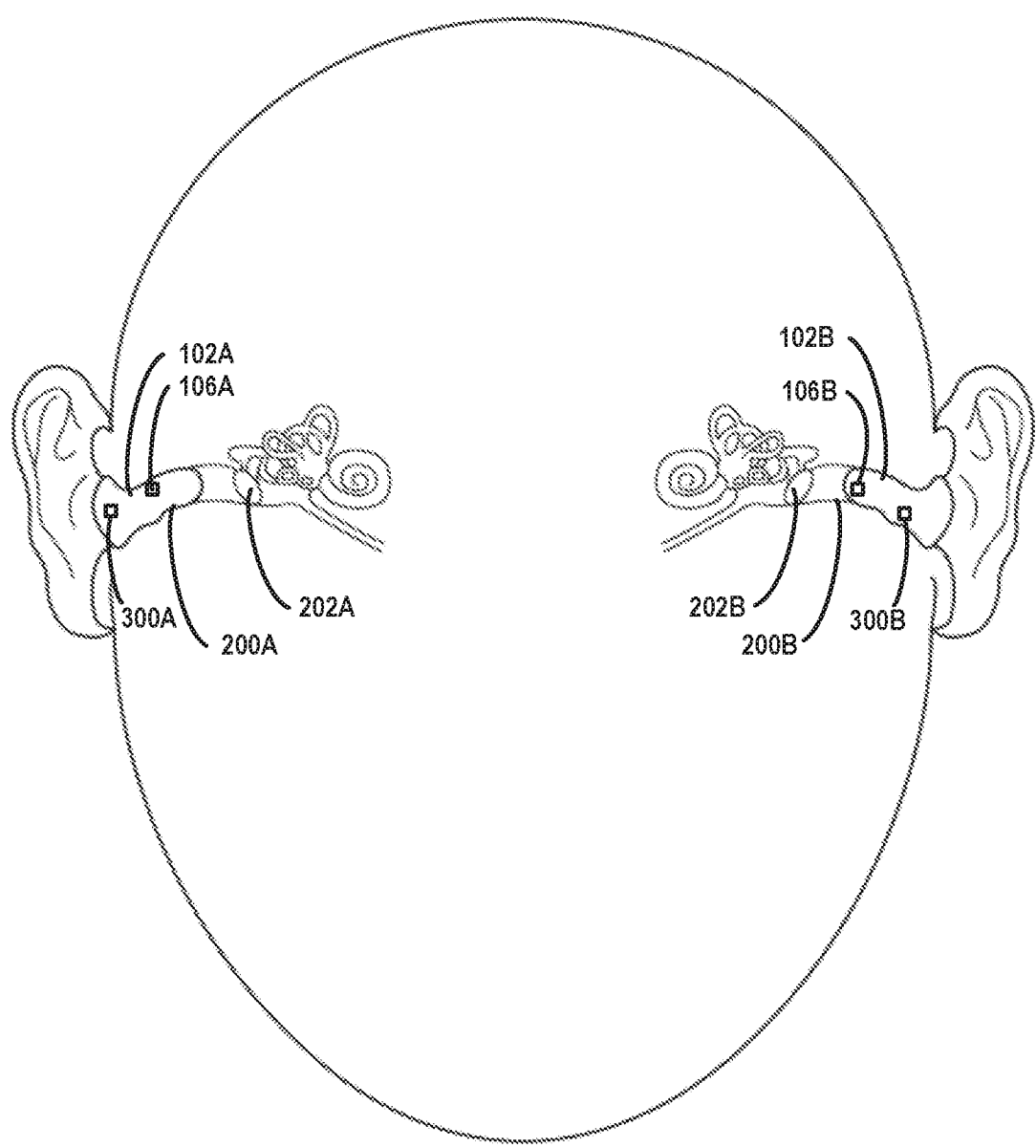
FIG. 3 is a conceptual diagram illustrating example hearing instruments having eye movement-related eardrum oscillation (EMREO) sensors and electrooculography (EOG) electrodes, in accordance with one or more techniques of this disclosure.

FIG. 3 is a conceptual diagram illustrating example hearing instruments 102 having EMREO sensors 106 and EOG electrodes 300A, 300B, in accordance with one or more techniques of this disclosure. This disclosure may refer to EOG electrodes 300 collectively as "EOG electrodes 300." In the example of FIG. 3, the processors of hearing instruments 102 and/or computing system 108 may use signals from the EOG electrodes 300 and also EMREO-related measurements from EMREO sensors 106 to generate information about the eye movements of user 104. For instance, in this example, EMREO sensors 106 may include microphones, VCSELs, ToF sensors, FSL sensors, PSL sensors, vibration sensors, implantable vibration sensors, or other types of sensors designed to generate EMREO-related measurements.

As shown in the example of FIG. 3, EOG electrodes 300 are positioned in the ears of user 104. As noted above, the electrical signals generated by in-ear EOG electrodes may be noisier than electrical signals generated by EOG electrodes closer to a person's eyes. However, in accordance with a technique of this disclosure, this problem may be overcome by using EMREO-related measurements to confirm eye movements detected using signals from in-ear EOG electrodes 300, or vice versa. For instance, if both the signals from EOG electrodes 300 and EMREO sensors 106 indicate an eye movement, there may be higher confidence that the eye movement in fact occurred. This may make the system as a whole more robust.

Furthermore, in some examples of this disclosure, the processors may use EMREO data in conjunction with data from EOG electrodes 300 and/or other sensors to provide a reference angle for one or more gyroscopes of one or more of hearing instruments 102.

Vibrometry is a technique for non-contact measurement and imaging of vibration of a surface. In the context of detecting eye movements, the surface may be the eardrums of user 104 or the skin of the external ear canal. The processors of hearing instruments 102 and/or computing system 108 may use vibrometry to detect oscillatory pressure waves caused by EMREOs on the skin of the external ear canal of user 104 in isolation of, or in conjunction with, sound-pressure level changes of EMREOs to select actions to perform, such as initiating or augmenting changes in the behavior of one or more of hearing instruments 102. For instance, the processors may use vibrometry to detect oscillatory pressure waves caused by EMREOs on the skin of the external ear canal or on the ossicular chain in isolation of, or in conjunction with, the sound-pressure level changes of EMREOs to initiate or augment changes in the behavior of a cochlear implant or other applications described in this disclosure.

EMREOs are likely triggered by contractions of the middle-ear muscles and subsequent flexing of the ossicular chain. Contraction of the middle ear muscles causes a damping of the transmission of sound to the inner ear, thereby attenuating incoming sounds. This occurs reflexively during loud sounds, presumably as a protective mechanism. Accordingly, in some examples, the processors may use EMREOs and/or vibrometry to limit the output of one or more of hearing instruments 102 when sound-evoked middle-ear muscle contractions are detected. For instance, the processors may reduce the gain of incoming sound and/or apply noise cancellation to further attenuate incoming sound.

In accordance with any of the examples of this disclosure, the processors of hearing instruments 102 and/or computing system 108 may create a mapping between sets of input data and one or more types of EMREO-related measurements of user 104. For instance, the types of EMREO-related measurements of user 104 may include the direction of the eye movements, magnitude of the eye movements, speed of the eye movements, and so on. The input data may include EMREO data (e.g., EMREO-related measurements or data generated based on EMREO-related measurements). In some examples, the input data may also include other types of data, such as EOG data. This mapping may increase the likelihood that the processors may detect individual eye movements more or less in real-time.

In some examples, the processors may use machine-learning to generate a mapping between the input data and the one or more types of information about the eye movements of user 104 (e.g., EMREO-related measurements). For instance, in some examples, the processors may implement an artificial neural network that takes the input data as an input vector and generates an output vector containing information about the eye movements of user 104. The neural network may be trained in one of various ways. For instance, in some examples, the neural network may initially be trained based on training data that includes input data and corresponding information about the eye movements of a plurality of people. In some such examples, to customize hearing instruments 102 to user 104, the neural network may later be refined based on input data and corresponding information about the eye movements of user 104. In other examples, the neural network may be trained only on input data and information about the eye movements of user 104.

Thus, ground-truth eye movement data may be collected via traditional camera-based or EOG approaches while synchronous EMREO data is recorded. The processors may use the ground-truth eye movement data as training data for machine learning algorithms that later predict information about the eye movements of user 104. With these data, a machine-learning algorithm may be trained to learn the relationship between EMREO data and eye movement. Training data may be collected across multiple users and multiple sessions for individual users to increase the robustness of the algorithm and the generalization of the solution to novel users, slight changes in hearing-aid position and different environmental contexts.

Furthermore, in some examples, user 104 may be able to help train the machine learning algorithms by providing feedback. This may be especially helping in the context of over-the-counter or direct-to-consumer hearing instruments. In such examples, while user 104 is wearing hearing instruments 102, user 104 may be prompted (e.g., by hearing instruments 102, another device, or a person) to move their eyes in particular directions and EMREO sensors 106 may generate corresponding EMREO-related measurements. Furthermore, in some examples, user 104 may provide feedback if the processors of hearing instruments 102 and/or computing system 108 select an incorrect action based on information about the eye movements of user 104. For instance, if the action selected by the processors corresponds to a rightward eye movement, but user 104 actually moved their eyes leftward or did not move their eyes, user 104 may provide feedback to the processors, which the processors may apply as another piece of training data By providing feedback in this manner, it may be unnecessary for user 104 to participate in a training session with a hearing professional in order to train the machine learning algorithms to generate information about the movements of the eyes of user 104.

In some examples, the processor may use signal-processing techniques to generate a mapping between the input data and the one or more types of information about the eye movements of user 104. For instance, in some examples, the signal-processing techniques may include be machine learning models that map of signals (which may include EMREO-related measurements) to a particular eye movement.

Such machine learning models may be trained according to standard machine learning techniques, such as backpropagation. In some examples, the processors may implement a threshold-based method in which the processors calculate and evaluate a statistic or set of statistics of the EMREO-related measurements to determine a particular eye movement. For instance, the processors may determine, based on a statistic regarding the EMREO-related data being greater than a particular threshold, that the eyes of user 102 have move a particular distance in a particular direction.

The processors of hearing instruments 102 and/or computing system 108 may use EMREO sensors 106 in one ear or both ears of user 104 to make EMREO-related measurements. Because both of eardrums 202 (FIG. 2) oscillate in sync when the eyes of user 104 move and because the information across that ears may be redundant, the processors may detect EMREOs using EMREO-related measurements from EMREO sensors in only a single ear of user 104. For instance, the processors may detect EMREOs based on EMREO-related measurements made by EMREO sensors 106A (and not EMREO sensors 106B, if EMREO sensors 106B are even included in hearing instrument 102B).

In other examples of this disclosure. EMREO sensors 106A and EMREO sensors 106B may generate EMREO-related measurements for both ears of user 104. For instance, in one such example, hearing instrument 102A may generate first EMREO data based on EMREO-related measurements generated by EMREO sensors 106A. In this example, hearing instrument 102A may communicate the first EMREO data to hearing instrument 102B. Furthermore, in this example, hearing instrument 102B may use the first EMREO data and EMREO-related measurements generated by EMREO sensors 106B to determine one or more actions. In this example, hearing instrument 102B may send instructions to hearing instrument 102A to perform the one or more actions. For instance, hearing instrument 102B may instruct hearing instrument 102A to adjust use a directional processing mode. In this example, the roles of hearing instrument 102A and hearing instrument 102B may be reversed.

In another example where EMREO sensors 106A and EMREO sensors 106B generate EMREO-related measurements for both ears of user 104, hearing instrument 102A may generate first EMREO data based on EMREO-related measurements generated by EMREO sensors 106A. Additionally, in this example, hearing instrument 102B may generate second EMREO data based on EMREO-related measurements generated by EMREO sensors 106B. In this example, hearing instrument 102A may communicate the first EMREO data to hearing instrument 102B and hearing instrument 102B may communicate the second EMREO data to hearing instrument 102A. Furthermore, in this example, hearing instrument 102B may use the first EMREO data and EMREO-related measurements generated by EMREO sensors 106B to determine and perform one or more actions. In this example, because each of hearing instruments 102 is able to determine the actions based on the same EMREO data, hearing instruments 102 may be able to identify and perform the actions without one of hearing instruments 102 instructing the other one of hearing instruments 102 to do so. For instance, hearing instruments 102 may each adjust to use a directional processing mode without one of hearing instruments 102 instructing the other to do so.

In another example where EMREO sensors 106A and EMREO sensors 106B generate EMREO-related measurements for both ears of user 102, hearing instrument 102A may generate first EMREO data based on EMREO-related data generated by EMREO sensors 106A. Additionally, in this example, hearing instrument 102B may generate second EMREO data based on EMREO-related data generated by EMREO sensors 106B. In this example, hearing instrument 102A may communicate the first EMREO data to computing system 108 and hearing instrument 102B may communicate the second EMREO data to computing system 108. Furthermore, in this example, computing system 108 may determine one or more actions. Computing system 108 may then instruct either or both of hearing instruments 102 to perform the actions.

Thus, in these examples, a set of processors may include a first set of processors and a second set of processors, where the first set of processors is in hearing instrument 102A and the second set of processors is in hearing instrument 102B. The first set of processors may receive first EMREO-related measurements from one or more EMREO sensors 106A of hearing instrument 102A. The second set of processors may receive second EMREO-related measurements from one or more EMREO sensors 106B of hearing instrument 102B. The one or more processors may perform an action, such as any of the actions described in examples of this disclosure, based on the first EMREO-related measurements and the second EMREO-related measurements. For instance, the processors may use the first EMREO-related measurement to confirm EMREOs corresponding to the second EMREO-related measurements, or vice versa. In some examples, a communication interface of the second hearing instrument may transmit data based on the second EMREO-related measurements to the first hearing instrument.

In any of the examples of communication between hearing instruments 102, the communication between hearing instrument 102A and hearing instrument 102B may be directly between hearing instrument 102A and hearing instrument 102B. In examples where hearing instruments 102 communicate directly, the communication between hearing instruments 102 may be wireless or non-wireless. Alternatively, in any of the examples of communication between hearing instruments 102, the communication between hearing instrument 102A and hearing instrument 102B may occur indirectly via one or more other computing devices or systems, such as computing system 108 (FIG. 1). In some examples where hearing instruments 102 communicate with computing system 108, one of hearing instruments 102 may communicate with computing system 108 by way of the other one of hearing instruments 102. In other examples where hearing instruments 102 communicate with computing system 108, each of hearing instruments 102 may communicate independently with computing system 108.

In examples where processors one of hearing instruments 102 receives EMREO data from the other one of hearing instruments 102 or processors of computing system 108 receives EMREO data from both of hearing instruments 102, the processors may apply signal processing techniques to enhance the EMREO data. This may increase the level of confidence in the determined presence and characteristics of EMREO. For instance, the processors may apply cross-correlation techniques for more reliable detection and to speed the analyses of the signals for faster changes to one or more of hearing instruments 102 based on the data.

Figure 4:
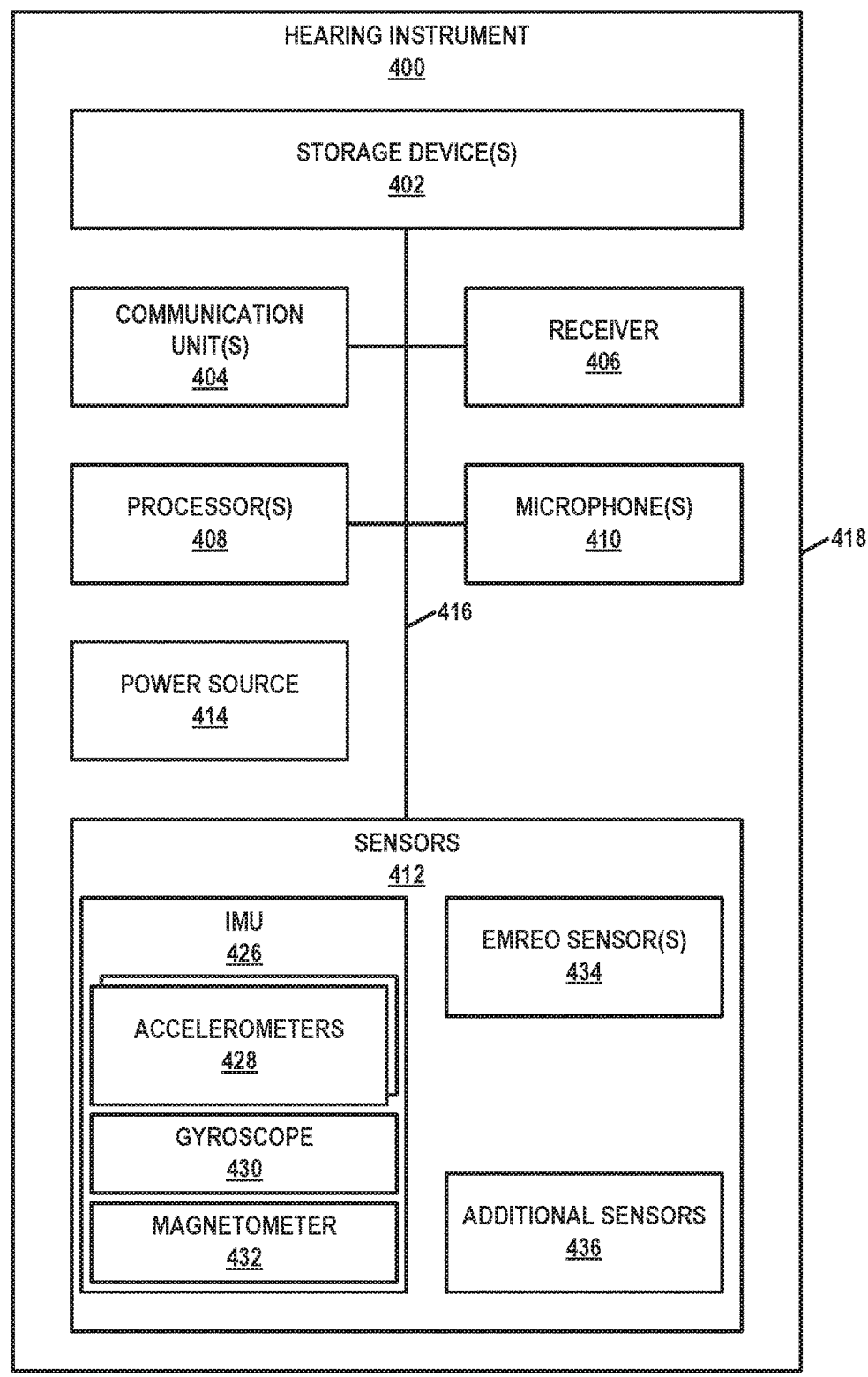
FIG. 4 is a block diagram illustrating example components of a hearing instrument, in accordance with one or more aspects of this disclosure.

FIG. 4 is a block diagram illustrating example components of hearing instrument 400, in accordance with one or more aspects of this disclosure. Hearing instrument 400 may be either one of hearing instruments 102. In the example of FIG. 4, hearing instrument 400 comprises one or more storage devices 402, one or more communication unit(s) 404, a receiver 406, one or more processor(s) 408, one or more microphone(s) 410, a set of sensors 412, a power source 414, and one or more communication channels 416. Communication channels 414 provide communication between storage devices 402, communication unit(s) 404, receiver 406, processor(s) 408, a microphone(s) 410, and sensors 412. Components 402, 404, 406, 408, 410, and 412 may draw electrical power from power source 414.

In the example of FIG. 4, each of components 402, 404, 406, 408, 410, 412, 414, and 416 are contained within a single housing 418. However, in other examples of this disclosure, components 402, 404, 406, 408, 410, 412, 414, and 416 may be distributed among two or more housings. For instance, in an example where hearing instrument 400 is a RIC device, receiver 406 and one or more of sensors 412 may be include in an in-ear housing separate from a behind-the-ear housing that contains the remaining components of hearing instrument 400. In such examples, a RIC cable may connect the two housings.

Furthermore, in the example of FIG. 4, sensors 412 include an IMU 426 that is configured to generate data regarding the motion of hearing instrument 400. IMU 426 may include a set of sensors. For instance, in the example of FIG. 4, IMU 426 includes one or more of accelerometers 428, a gyroscope 430, a magnetometer 432, combinations thereof, and/or other sensors for determining the motion of hearing instrument 400.

Additionally, in the example of FIG. 4, sensors 412 also include EMREO sensors 434. EMREO sensors 434 may be either EMREO sensors 106A or EMREO sensors 106B, as described elsewhere in this disclosure. Furthermore, in the example of FIG. 4, hearing instrument 400 may include one or more additional sensors 436. Additional sensors 436 may include EOG electrodes 300A, 300B (FIG. 3), a photoplethysmography (PPG) sensor, blood oximetry sensors, blood pressure sensors, electrocardiograph (EKG) sensors, body temperature sensors, electroencephalography (EEG) sensors, environmental temperature sensors, environmental pressure sensors, environmental humidity sensors, skin galvanic response sensors, and/or other types of sensors. In other examples, hearing instrument 400 and sensors 412 may include more, fewer, or different components.

Storage devices 402 may store data. Storage devices 402 may comprise volatile memory and may therefore not retain stored contents if powered off. Examples of volatile memories may include random access memories (RAM), dynamic random access memories (DRAM), static random access memories (SRAM), and other forms of volatile memories known in the art. Storage devices 402 may further be configured for long-term storage of information as non-volatile memory space and retain information after power on/off cycles. Examples of non-volatile memory configurations may include magnetic hard discs, optical discs, floppy discs, flash memories, or forms of electrically programmable memories (EPROM) or electrically erasable and programmable (EEPROM) memories.

Communication unit(s) 404 may enable hearing instrument 400 to send data to and receive data from one or more other devices, such as another hearing instrument, an accessory device, a mobile device, or another types of device. Communication unit(s) 404 may enable hearing instrument 400 using wireless or non-wireless communication technologies. For instance, communication unit(s) 404 enable hearing instrument 400 to communicate using one or more of various types of wireless technology, such as a BLUETOOTH™ technology, 3G, 4G, 4G LTE, 5G, ZigBee, WI-FI™, Near-Field Magnetic Induction (NFMI), ultrasonic communication, infrared (IR) communication, or another wireless communication technology. In some examples, communication unit(s) 404 may enable hearing instrument 400 to communicate using a cable-based technology, such as a Universal Serial Bus (USB) technology.

Receiver 406 comprises one or more speakers for generating audible sound. Microphone(s) 410 detects incoming sound and generates one or more electrical signals (e.g., an analog or digital electrical signal) representing the incoming sound. Processor(s) 408 may be processing circuits configured to perform various activities. For example, processor(s) 408 may process the signal generated by microphone(s) 410 to enhance, amplify, or cancel-out particular channels within the incoming sound. Processor(s) 408 may then cause receiver 406 to generate sound based on the processed signal. In some examples, processor(s) 408 include one or more digital signal processors (DSPs). In some examples, processor(s) 408 may cause communication unit(s) 404 to transmit one or more of various types of data. For example, processor(s) 408 may cause communication unit(s) 404 to transmit data to computing system 108. Furthermore, communication unit(s) 404 may receive audio data from computing system 108 and processor(s) 408 may cause receiver 406 to output sound based on the audio data.

In accordance with one or more techniques of this disclosure, processor(s) 408 may obtain one or more signals generated by one or more sensors (e.g., EMREO sensor(s) 434 and, in some examples, one or more additional sensors 436) of hearing instrument 400 that are located within an ear canal of a user (e.g., user 104) of hearing instrument 400. Processor(s) 408 may perform one or more actions based on the one or more signals being indicative of an occurrence of EMREOs of an eardrum of the user of hearing instrument 400. For instance, processor(s) 408 may perform actions as describe in any of the examples provided elsewhere in this disclosure.

In some examples, hearing instrument 102 is a "plug-n-play" type of device. In some examples, hearing instrument 102 is programmable to help the user manage things like wind noise. Furthermore, in some examples, hearing instrument 102 comprises a custom earmold or a standard receiver module at the end of a RIC cable. The additional volume in a custom earmold may allow room for components such as sensors (accelerometers, heartrate monitors, temp sensors), a woofer-tweeter, and an acoustic valve that provides occlusion when desired. In some examples, a six conductor RIC cable is used for in hearing instruments with sensors, woofer-tweeters, and/or acoustic valves.

Figure 5:
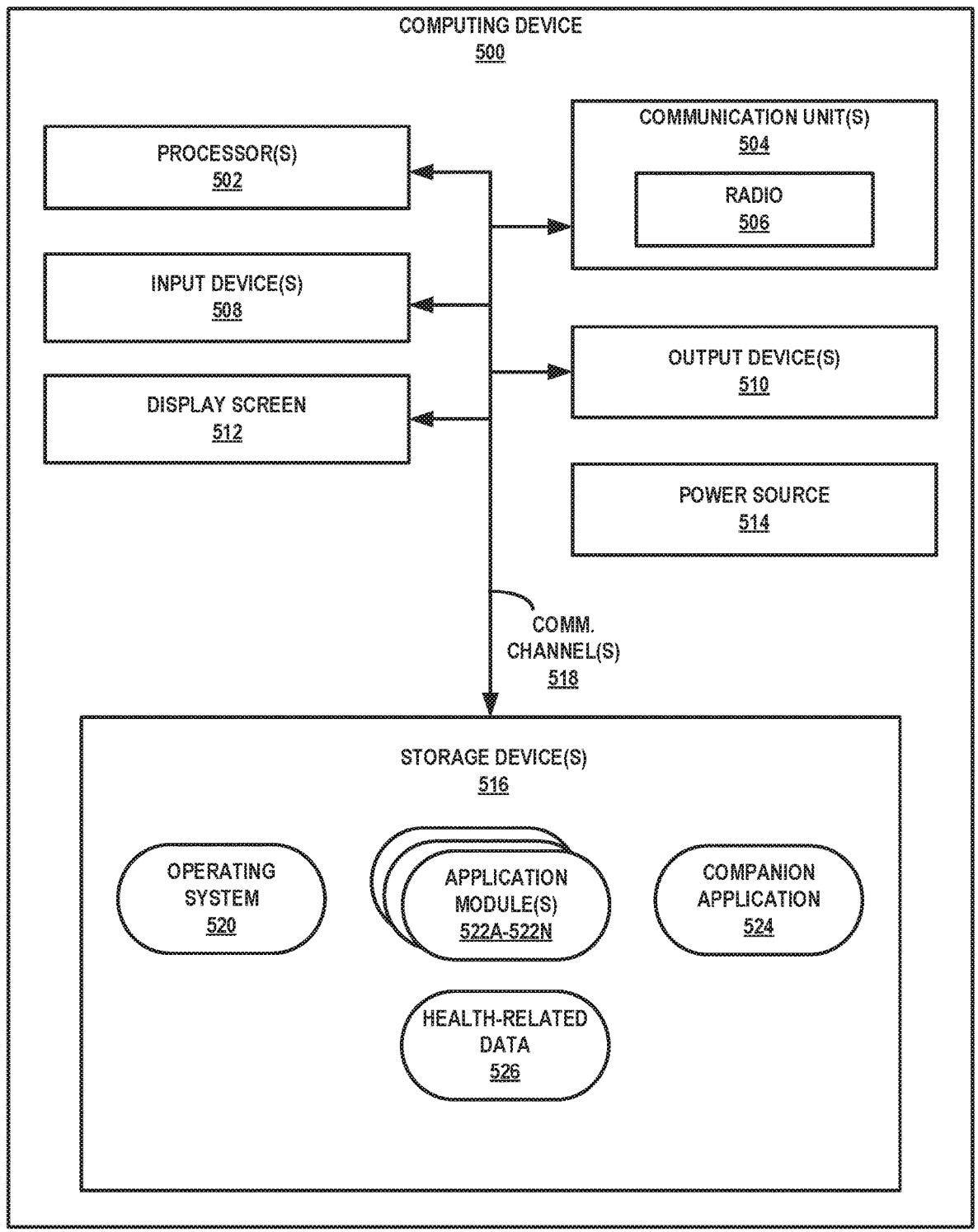
FIG. 5 is a block diagram illustrating example components of a computing device, in accordance with one or more aspects of this disclosure.

FIG. 5 is a block diagram illustrating example components of computing device 500, in accordance with one or more aspects of this disclosure. FIG. 5 illustrates only one particular example of computing device 500, and many other example configurations of computing device 500 exist. Computing device 500 may be a computing device in computing system 108 (FIG. 1).

As shown in the example of FIG. 5, computing device 500 includes one or more processor(s) 502, one or more communication unit(s) 504, one or more input device(s) 508, one or more output device(s) 510, a display screen 512, a power source 514, one or more storage device(s) 516, and one or more communication channels 518. Computing device 500 may include other components. For example, computing device 500 may include physical buttons, microphones, speakers, communication ports, and so on. Communication channel(s) 518 may interconnect each of components 502, 504, 508, 510, 512, and 516 for inter-component communications (physically, communicatively, and/or operatively). In some examples, communication channel(s) 518 may include a system bus, a network connection, an inter-process communication data structure, or any other method for communicating data. Power source 514 may provide electrical energy to components 502, 504, 508, 510, 512 and 516.

Storage device(s) 516 may store information required for use during operation of computing device 500. In some examples, storage device(s) 516 have the primary purpose of being a short term and not a long-term computer-readable storage medium. Storage device(s) 516 may be volatile memory and may therefore not retain stored contents if powered off. Storage device(s) 516 may further be configured for long-term storage of information as non-volatile memory space and retain information after power on/off cycles. In some examples, processor(s) 502 on computing device 500 read and may execute instructions stored by storage device(s) 516.

Computing device 500 may include one or more input device(s) 508 that computing device 50X) uses to receive user input. Examples of user input include tactile, audio, and video user input. Input device(s) 508 may include presence-sensitive screens, touch-sensitive screens, mice, keyboards, voice responsive systems, microphones or other types of devices for detecting input from a human or machine.

Communication unit(s) 504 may enable computing device 500 to send data to and receive data from one or more other computing devices (e.g., via a communications network, such as a local area network or the Internet). For instance, communication unit(s) 504 may be configured to receive source data exported by hearing instrument(s) 102, receive comment data generated by user 112 of hearing instrument(s) 102, receive and send request data, receive and send messages, and so on. In some examples, communication unit(s) 504 may include wireless transmitters and receivers that enable computing device 500 to communicate wirelessly with the other computing devices. For instance, in the example of FIG. 5, communication unit(s) 504 include a radio 506 that enables computing device 500 to communicate wirelessly with other computing devices, such as hearing instruments 102 (FIG. 1). Examples of communication unit(s) 504 may include network interface cards, Ethernet cards, optical transceivers, radio frequency transceivers, or other types of devices that are able to send and receive information. Other examples of such communication units may include BLUETOOTH™, 3G, 4G, 5G, and WI-FI™ radios, Universal Serial Bus (USB) interfaces, etc. Computing device 500 may use communication unit(s) 504 to communicate with one or more hearing instruments (e.g., hearing instrument 102 (FIG. 1, FIG. 4)). Additionally, computing device 500 may use communication unit(s) 504 to communicate with one or more other remote devices.

Output device(s) 510 may generate output. Examples of output include tactile, audio, and video output. Output device(s) 510 may include presence-sensitive screens, sound cards, video graphics adapter cards, speakers, liquid crystal displays (LCD), or other types of devices for generating output.

Processor(s) 502 may read instructions from storage device(s) 516 and may execute instructions stored by storage device(s) 516. Execution of the instructions by processor(s) 502 may configure or cause computing device 500 to provide at least some of the functionality ascribed in this disclosure to computing device 500. As shown in the example of FIG. 5, storage device(s) 516 include computer-readable instructions associated with operating system 520, application modules 522A-522N (collectively, "application modules 522"), and a companion application 524. Additionally, in the example of FIG. 5, storage device(s) 516 may store health-related data 526.

Execution of instructions associated with operating system 520 may cause computing device 500 to perform various functions to manage hardware resources of computing device 500 and to provide various common services for other computer programs. Execution of instructions associated with application modules 522 may cause computing device 500 to provide one or more of various applications (e.g., "apps," operating system applications, etc.). Application modules 522 may provide particular applications, such as text messaging (e.g., SMS) applications, instant messaging applications, email applications, social media applications, text composition applications, and so on.

Execution of instructions associated with companion application 524 by processor(s) 502 may cause computing device 500 to perform one or more of various functions. For example, execution of instructions associated with companion application 524 may cause computing device 500 to configure communication unit(s) 504 to receive data from hearing instruments 102 and use the received data to present health-related data to a user, such as user 104 or a third-party user. In some examples, companion application 524 is an instance of a web application or server application. In some examples, such as examples where computing device 500 is a mobile device or other type of computing device, companion application 524 may be a native application.

In some examples of this disclosure, processor(s) 502 are configured to obtain, one or more signals generated by one or more sensors (e.g., EMREO sensor(s) 434 and, in some examples, one or more additional sensors 436) of one or more hearing instruments (e.g., one or more of hearing instruments 102) that are located within one or more ear canals of a user (e.g., user 104) of the one or more hearing instruments. In other words, processor(s) 502 may obtain EMREO-related measurements from one or more EMREO sensors of a hearing instrument. Processor(s) 502 may perform one or more actions based on the EMREO-related measurements, such as when the EMREO-related measurements are being indicative of an occurrence of EMREOs of one or more eardrums of the user of the one or more hearing instruments. In some examples, rather than receiving EMREO-related measurements directly, processor(s) 502 may receive data generated based on the EMREO-related measurements and perform one or more actions based on the received data. For instance, processor(s) 502 may perform actions as describe in any of the examples provided elsewhere in this disclosure.

Figure 6:
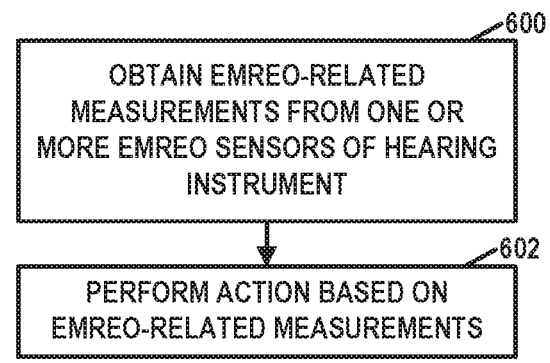
FIG. 6 is a flowchart illustrating an example operation in accordance with one or more example techniques described in this disclosure.

FIG. 6 is a flowchart illustrating an example operation 600 of this disclosure. Other examples of this disclosure may include more, fewer, or different actions. In the example of FIG. 6, a set of one or more processors (i.e., processing circuits) may obtain EMREO-related measurements from one or more EMREO sensors (e.g., EMREO sensors 106A or EMREO sensors 106B) of a hearing instrument (e.g., hearing instrument 102A or hearing instrument 102B) (600). The EMREO sensors may be located in an ear canal of a user (e.g., user 104) of the hearing instrument and are configured to detect environmental signals of EMREOs of an eardrum of the user of the hearing instrument and generate the EMREO-related measurements based on the detected environmental signals. For instance, in examples where the EMREO sensors include microphones, the microphones may generate signals based on changes in air pressure caused by EMREOs; in examples where the EMREO sensors include a VCSEL and a photodetector, the photodetector may generate EMREO-related measurements that indicate a position of an eardrum; and so on as described elsewhere in this disclosure. The set of processors may include one or more processors of hearing instruments 102 and/or one or more processors of computing system 108. Thus, in some examples, the hearing instrument includes each of the processors. In other examples, the hearing instrument includes one or more of processors and one or more other devices (e.g., a device of computing system 108, another hearing instrument, etc.) include one or more of the processors.

Furthermore, in the example of FIG. 6, the one or more processors may perform an action based on the EMREO-related measurements (602). For instance, example actions may include any of the actions described elsewhere in this disclosure with respect to the various use cases, or combinations thereof.

In this disclosure, ordinal terms such as "first," "second," "third," and so on, are not necessarily indicators of positions within an order, but rather may be used to distinguish different instances of the same thing. Examples provided in this disclosure may be used together, separately, or in various combinations. Furthermore, with respect to examples that involve personal data regarding a user, it may be required that such personal data only be used with the permission of the user.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processing circuits to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, cache memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Functionality described in this disclosure may be performed by fixed function and/or programmable processing circuitry. For instance, instructions may be executed by fixed function and/or programmable processing circuitry. Such processing circuitry may include one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements. Processing circuits may be coupled to other components in various ways. For example, a processing circuit may be coupled to other components via an internal device interconnect, a wired or wireless network connection, or another communication medium.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

Various examples have been described. These and other examples are within the scope of the following claims.

What is claimed is:

1. A method comprising:
   obtaining, by a set of one or more processing circuits, eye movement-related eardrum oscillation (EMREO)-related measurements from one or more EMREO sensors of a hearing instrument, wherein the EMREO sensors are located in an ear canal of a user of the hearing instrument and are configured to detect environmental signals of EMREOs of an eardrum of the user of the hearing instrument and generate the EMREO-related measurements based on the detected environmental signals, wherein:
   the one or more EMREO sensors include a first microphone positioned at a medial tip of the hearing instrument and configured to detect changes in air pressure within the ear canal caused by EMREOs,
   the EMREO-related measurements include a signal generated by the first microphone, and
   the hearing instrument comprises a second microphone positioned at a lateral surface of the hearing instrument;
   generating, by the one or more processing circuits, based on a comparison of the signal generated by the first microphone and a signal generated by the second microphone, an enhanced version of the signal generated by the first microphone; and
   performing, by the one or more processing circuits, an action based on the enhanced version of the signal generated by the first microphone.

2. The method of claim 1, wherein the hearing instrument includes each of the one or more processing circuits.

3. The method of claim 1, wherein:
   the signal generated by the first microphone is a first signal and the signal generated by the second microphone is a second signal,
   the one or more EMREO sensors include a third microphone,
   the third microphone is positioned within the ear canal of the user and configured to detect changes in air pressure within the ear canal caused by EMREOs,
   the EMREO-related measurements include a third signal produced by the third microphone,
   the method further comprises applying, by the one or more processing circuits, a beamformer to the first signal and the third signal to generate a fourth signal, wherein a focal direction of the beamformer is toward the eardrum of the user of the hearing instrument, and
   generating the enhanced version of signal generated by the first microphone comprises generating, by the one or more processing circuits, based on a comparison of the fourth signal and the signal generated by the second microphone, the enhanced version of the signal generated by the first microphone.

4. The method of claim 1, wherein at least one of:
   the EMREO sensors include a vertical-cavity surface-emitting laser (VCSEL) positioned to shine a coherent beam onto the eardrum; and obtaining the EMREO-related measurements comprises applying, by the one or more processing circuits, optical feedback interferometry based on reflected light of the coherent beam to determine a position of the eardrum,
   the EMREO sensors include a time of flight (ToF) sensor configured to emit infrared light toward the eardrum and configured to determine a distance to the eardrum based on a travel time of the infrared light to the eardrum and back to the ToF sensor, and obtaining the EMREO-related measurements comprises determining, by the one or more processing circuits, the position of the eardrum based on the travel time,
   the EMREO sensors include a structured light sensor configured to emit structured light toward the eardrum, and obtaining the EMREO-related measurements comprises determining, by the one or more processing circuits, the position of the eardrum based on a pattern of light detected by the structured light sensor,
the EMREO sensors include a vibration sensor in contact with skin of the ear canal, and obtaining the EMREO-related measurements comprises obtaining, by the one or more processing circuits, measurements of surface waves in the skin of the ear canal caused by the EMREOs of the eardrum, or
the EMREO sensors include a vibration sensor attached to the eardrum or an ossicular chain of the user, and obtaining the EMREO-related measurements comprises obtaining, by the one or more processing circuits, measurements of vibrations from the vibration sensor.

5. The method of claim 1, wherein:
the hearing instrument comprises an array of external microphones configured to receive sound from an environment of the user of the hearing instrument, and
performing the action comprises:
  determining, by the one or more processing circuits, a focal direction based on the EMREO-related measurements; and
  applying, by the one or more processing circuits, a beamformer to signals generated by the external microphones, wherein the beamformer has the determined focal direction.

6. The method of claim 1, wherein:
the hearing instrument is a first hearing instrument,
the EMREO-related measurements are first EMREO-related measurements,
the eardrum is a first eardrum of the user,
the ear canal is a first ear canal of the user,
the set of processing circuits includes a first set of processing circuits and a second set of processing circuits, the first set of processing circuits being in the first hearing instrument, and the second set of processing circuits being in a second hearing instrument of the user,
obtaining the EMREO-related measurements further comprises obtaining, by the second set of processing circuits, second EMREO-related measurements from one or more EMREO sensors of the second hearing instrument, the EMREO sensors of the second hearing instrument are located in a second ear canal of the user and are configured to detect environmental signals of EMREOs of a second eardrum of the user,
performing the action comprises performing, by the one or more processing circuits, the action based on the first EMREO-related measurements and the second EMREO-related measurements.

7. The method of claim 6, further comprising transmitting, by a communication interface of the second hearing instrument, data based on the second EMREO-related measurements to the first hearing instrument.

8. The method of claim 1, wherein the performing the action comprises at least one of:
  generating, by the one or more processing circuits, based on the EMREO-related measurements, data regarding sleep of the user,
  determining, by the one or more processing circuits, based on the EMREO-related measurements, a salient object in an environment of the user, or
  determining, by the one or more processing circuits, user input to a user interface based on the EMREO-related measurements.

9. The method of claim 1, wherein performing the action comprises:
  determining, by the one or more processing circuits, an interpersonal message based on the EMREO-related measurements; and
  sending, by the one or more processing circuits, the interpersonal message.

10. The method of claim 1, wherein performing the action comprises detecting, by the one or more processing circuits, based on the EMREO-related measurements, an epileptic seizure of the user.

11. The method of claim 1, wherein performing the action comprises:
  determining, by the one or more processing circuits, based on the EMREO-related measurements, potential modifications to left-ear and right-ear audio signals; and
  applying, by the one or more processing circuits, the potential modifications to the left-ear and right-ear audio signals in response to determining a movement of a head of the user.

12. A system comprising:
one or more eye movement-related eardrum oscillation (EMREO) sensors located in an ear canal of a user of a hearing instrument, wherein the EMREO sensors are configured to detect environmental signals of EMREOs of an eardrum of the user and generate EMREO-related measurements based on the detected environmental signals, wherein:
  the one or more EMREO sensors include a first microphone positioned at a medial tip of the hearing instrument and configured to detect changes in air pressure within the ear canal caused by EMREOs, and
  the hearing instrument comprises a second microphone positioned at a lateral surface of the hearing instrument; and
one or more processing circuits configured to:
  obtain the EMREO-related measurements from the one or more EMREO sensors, the EMREO-related measurements including a signal generated by the first microphone;
  generate, based on a comparison of the signal generated by the first microphone and a signal generated by the second microphone, an enhanced version of the signal generated by the first microphone; and
  perform an action based on the enhanced version of the signal generated by the first microphone.

13. The system of claim 12, wherein the system comprises the hearing instrument and the hearing instrument comprises at least one of the EMREO sensors or the one or more processing circuits.

14. The system of claim 12, wherein:
the system comprises a computing system and the hearing instrument, and
the computing system comprises the one or more processing circuits.

15. The system of claim 12, wherein:
the signal generated by the first microphone is a first signal and the signal generated by the second microphone is a second signal,
the one or more EMREO sensors include a third microphone,
the third microphone is positioned within the ear canal of the user and configured to detect changes in air pressure within the ear canal caused by EMREOs,
the EMREO-related measurements include a third signal produced by the third microphone,
the one or more processing circuits are configured to apply a beamformer to the first signal and the third signal to generate a fourth signal, wherein a focal direction of the beamformer is toward the eardrum of the user of the hearing instrument, and the one or more processing circuits are configured such that, as part of generating the enhanced version of signal generated by the first microphone, the one or more processing circuits generate, based on a comparison of the fourth signal and the signal generated by the second microphone, the enhanced version of the signal generated by the first microphone.

16. The system of claim 12, wherein at least one of:

the EMREO sensors include a vertical-cavity surface-emitting laser (VCSEL) positioned to shine a coherent beam onto the eardrum, and the one or more processing circuits are configured such that, as part of obtaining the EMREO-related measurements, the one or more processing circuits apply optical feedback interferometry based on reflected light of the coherent beam to determine a position of the eardrum, the EMREO sensors include a time of flight (ToF) sensor configured to emit infrared light toward the eardrum and configured to determine a distance to the eardrum based on a travel time of the infrared light to the eardrum and back to the ToF sensor, and the one or more processing circuits are configured such that, as part of obtaining the EMREO-related measurements, the one or more processing circuits determine the position of the eardrum based on the travel time, the EMREO sensors include a structured light sensor configured to emit structured light toward the eardrum, and the one or more processing circuits are configured such that, as part of obtaining the EMREO-related measurements, the one or more processing circuits determine the position of the eardrum based on a pattern of light detected by the structured light sensor, the EMREO sensors include a vibration sensor in contact with skin of the ear canal, the one or more processing circuits are configured such that, as part of obtaining the EMREO-related measurements, the one or more processing circuits obtain measurements of surface waves in the skin of the ear canal caused by the EMREOs of the eardrum, or the EMREO sensors include a vibration sensor attached to the eardrum or an ossicular chain of the user, and the one or more processing circuits are configured such that, as part of obtaining the EMREO-related measurements, the one or more processing circuits obtain measurements of vibrations from the vibration sensor.

17. The system of claim 12, wherein:

the hearing instrument comprises an array of external microphones configured to receive sound from an environment of the user of the hearing instrument, and the one or more processing circuits are configured such that, as part of performing the action, the one or more processing circuits:

determine a focal direction based on the EMREO-related measurements; and apply a beamformer to signals generated by the external microphones, wherein the beamformer has the determined focal direction.

18. The system of claim 12, wherein:

the hearing instrument is a first hearing instrument, the EMREO-related measurements are first EMREO-related measurements, the eardrum is a first eardrum of the user, the ear canal is a first ear canal of the user, the first hearing instrument comprises a communication interface configured to receive data based on second EMREO-related measurements from one or more EMREO sensors of a second hearing instrument, the EMREO sensors of the second hearing instrument being located in a second ear canal of the user and configured to detect environmental signals of EMREOs of a second eardrum of the user, and the one or more processing circuits are configured to perform the action based on the first EMREO-related measurements and the data based on the second EMREO-related measurements.

19. The system of claim 12, wherein at least one of:

the one or more processing circuits are configured such that, as part of performing the action, the one or more processing circuits generate, based on the EMREO-related measurements, data regarding sleep of the user, the one or more processing circuits are configured such that, as part of performing the action, the one or more processing circuits determine, based on the EMREO-related measurements, a salient object in an environment of the user, or wherein the one or more processing circuits are configured such that, as part of performing the action, the one or more processing circuits determine user input to a user interface based on the EMREO-related measurements.

20. The system of claim 12, wherein the one or more processing circuits are configured such that, as part of performing the action, the one or more processing circuits:

determine an interpersonal message based on the EMREO-related measurements; and send the interpersonal message.

21. The system of claim 12, wherein the one or more processing circuits are configured such that, as part of performing the action, the one or more processing circuits detect, based on the EMREO-related measurements, an epileptic seizure of the user.

22. The system of claim 12, wherein the one or more processing circuits are configured such that, as part of performing the action, the one or more processing circuits:

determine, based on the EMREO-related measurements, potential modifications to left-ear and right-ear audio signals; and apply the potential modifications to the left-ear and right-ear audio signals in response to determining a movement of a head of the user.

23. A non-transitory computer-readable storage medium having instructions stored thereon that, when executed, cause one or more processing circuits to:

obtain eye movement-related eardrum oscillation (EMREO)-related measurements from one or more EMREO sensors of a hearing instrument, wherein the EMREO sensors are located in an ear canal of a user of the hearing instrument and are configured to detect environmental signals of EMREOs of an eardrum of the user of the hearing instrument and generate the EMREO-related measurements based on the detected environmental signals, wherein:

the one or more EMREO sensors include a first microphone positioned at a medial tip of the hearing instrument and configured to detect changes in air pressure within the ear canal caused by EMREOs, the EMREO-related measurements include a signal generated by the first microphone, and the hearing instrument comprises a second microphone positioned at a lateral surface of the hearing instrument;

generate, based on a comparison of the signal generated by the first microphone and a signal generated by the second microphone, an enhanced version of the signal generated by the first microphone; and perform an action based on the enhanced version of the signal generated by the first microphone.

24. A method comprising:

obtaining, by a set of one or more processing circuits, eye movement-related eardrum oscillation (EMREO)-related measurements from one or more EMREO sensors of a hearing instrument, wherein the EMREO sensors are located in an ear canal of a user of the hearing instrument and are configured to detect environmental signals of EMREOs of an eardrum of the user of the hearing instrument and generate the EMREO-related measurements based on the detected environmental signals, wherein the EMREO sensors include a vibration sensor in contact with skin of the ear canal, and the EMREO-related measurements include measurements of surface waves in the skin of the ear canal caused by the EMREOs of the eardrum;

determining, by the one or more processing circuits, based on the measurements of the surface waves in the skin of the ear canal caused by the EMREOs of the eardrum, a direction of eye movement of the user; and performing, by the one or more processing circuits, an action based on the direction of eye movement of the user.

25. A system comprising:

one or more eye movement-related eardrum oscillation (EMREO) sensors located in an ear canal of a user of a hearing instrument, wherein the EMREO sensors are configured to detect environmental signals of EMREOs of an eardrum of the user and generate EMREO-related measurements based on the detected environmental signals, the EMREO sensors include a vibration sensor in contact with skin of the ear canal; and one or more processing circuits configured to:
  obtain the EMREO-related measurements from the one or more EMREO sensors, wherein the EMREO-related measurements include measurements of surface waves in the skin of the ear canal caused by the EMREOs of the eardrum;
  determine, based on the measurements of the surface waves in the skin of the ear canal caused by the EMREOs of the eardrum, a direction of eye movement of the user; and
  perform an action based on the direction of eye movement of the user.

* * * * *